United States Patent
Gelfand et al.

(10) Patent No.: US 9,206,476 B2
(45) Date of Patent: Dec. 8, 2015

(54) SEQUENCING AND GENOTYPING USING REVERSIBLY TERMINATING NUCLEOTIDES

(75) Inventors: David H. Gelfand, Oakland, CA (US); Amar Gupta, Danville, CA (US)

(73) Assignee: ROCHE MOLECULAR SYSTEMS, INC, Pleasanton, CA (US)

( * ) Notice: Subject to any disclaimer, the term of this patent is extended or adjusted under 35 U.S.C. 154(b) by 1670 days.

(21) Appl. No.: 12/158,257

(22) PCT Filed: Dec. 20, 2006

(86) PCT No.: PCT/US2006/048933
§ 371 (c)(1),
(2), (4) Date: Jun. 19, 2008

(87) PCT Pub. No.: WO2007/075967
PCT Pub. Date: Jul. 5, 2007

(65) Prior Publication Data
US 2008/0293071 A1    Nov. 27, 2008

Related U.S. Application Data

(60) Provisional application No. 60/752,827, filed on Dec. 21, 2005, provisional application No. 60/844,041, filed on Sep. 11, 2006.

(51) Int. Cl.
*C12Q 1/68* (2006.01)

(52) U.S. Cl.
CPC .................................. *C12Q 1/6869* (2013.01)

(58) Field of Classification Search
None
See application file for complete search history.

(56) References Cited

U.S. PATENT DOCUMENTS

| | | | |
|---|---|---|---|
| 5,436,143 A * | 7/1995 | Hyman | 435/91.2 |
| 5,532,130 A | 7/1996 | Alul | |
| 2005/0037398 A1 | 2/2005 | Gelfand et al. | |
| 2007/0154914 A1 | 7/2007 | Gelfand et al. | |

FOREIGN PATENT DOCUMENTS

| | | | | |
|---|---|---|---|---|
| EP | 2007008997 | | 10/2007 | |
| GB | WO2005/118608 | * | 12/2005 | C07H 19/04 |
| WO | WO00/53805 | * | 9/2000 | C12Q 1/68 |
| WO | 2005005667 A2 | | 1/2005 | |
| WO | 2005005667 A3 | | 1/2005 | |
| WO | WO2005026184 | * | 3/2005 | C07H 19/00 |
| WO | 2005118608 A2 | | 12/2005 | |
| WO | 2005118608 A3 | | 12/2005 | |
| WO | WO2005/118608 | * | 12/2005 | C07H 19/00 |
| WO | 2007075967 A2 | | 7/2007 | |
| WO | 2007075967 A3 | | 7/2007 | |

OTHER PUBLICATIONS

D'Abramo et al. (2004, J. Molec. Bio., 2004, 337(1):1-14).*
Hamel et al. (PNAS, 1981, 78(6):3368-72).*
Didenko et al. (Biotechniques, 2001, 31(5):1106-1121).*
Murphy et al. (Am. J. Path., 2002, 161(1):27-33).*
Astatke et al. (PNAS, 1998, vol. 95: p. 3402-3407).*
Zhang, Jia, et al., 2005 "Proofreading genotyping assays mediated by high fidelity exo + DNA polymerases", Trends in Biotechnology, 23(2):92-96.
Metzker, ML, "Emerging technologies in DNA sequencing", Genome Res. 2005, 15: 1767-1776.

* cited by examiner

*Primary Examiner* — Stephanie K Mummert
(74) *Attorney, Agent, or Firm* — David J. Chang

(57) ABSTRACT

The invention provides a method of determining the nucleotide sequence of a target nucleic acid using a reversibly terminating nucleotide that is modified at the 2' position.

21 Claims, 5 Drawing Sheets

Figure 1
Fig. 1A
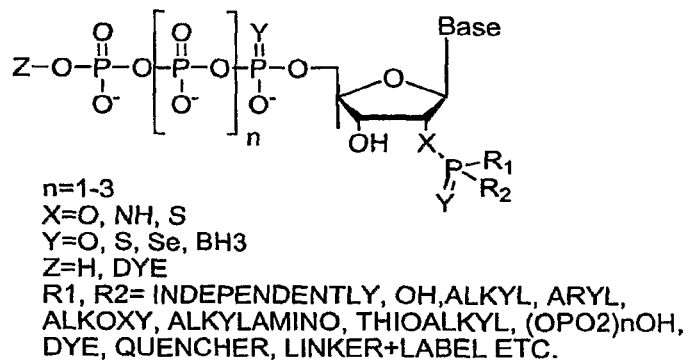
n=1-3
X=O, NH, S
Y=O, S, Se, BH3
Z=H, DYE
R1, R2= INDEPENDENTLY, OH, ALKYL, ARYL,
ALKOXY, ALKYLAMINO, THIOALKYL, (OPO2)nOH,
DYE, QUENCHER, LINKER+LABEL ETC.
Fig. 1B
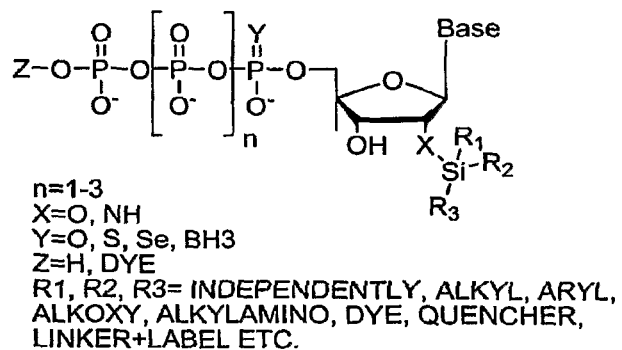
n=1-3
X=O, NH
Y=O, S, Se, BH3
Z=H, DYE
R1, R2, R3= INDEPENDENTLY, ALKYL, ARYL,
ALKOXY, ALKYLAMINO, DYE, QUENCHER,
LINKER+LABEL ETC.
Fig. 1C
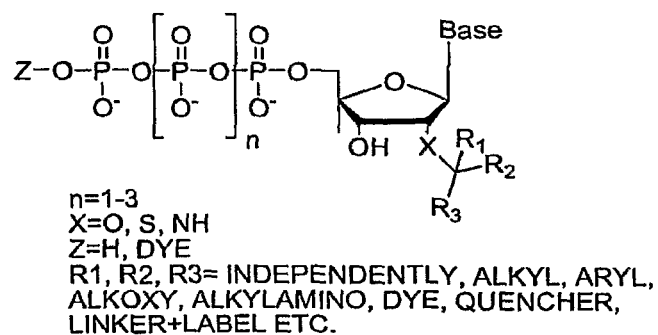
n=1-3
X=O, S, NH
Z=H, DYE
R1, R2, R3= INDEPENDENTLY, ALKYL, ARYL,
ALKOXY, ALKYLAMINO, DYE, QUENCHER,
LINKER+LABEL ETC.

n=1-3
Y=O, S, Se, BH3
Z=H, DYE
R= ALKYL, ARYL, DYE, QUENCHER, LABEL ETC.

n=1-3
X=O, S, NH
Y=O,S,SE, BH3
Z=H, DYE
R1, R2, R3= INDEPENDENTLY, ALKYL, ARYL, ALKOXY, ALKYLAMINO, DYE, QUENCHER, LINKER+LABEL ETC.

n=1-3
Y=O, S, Se, BH3
Z=H, DYE
R= ALKYL, ARYL, DYE, QUENCHER, LABEL ETC.

X=O, NH, S

X=O, NH, S

SEQUENCE LISTING

```
<160> NUMBER OF SEQ ID NOS: 3

<210> SEQ ID NO 1
<211> LENGTH: 32
<212> TYPE: RNA
<213> ORGANISM: Artificial Sequence
<220> FEATURE:
<223> OTHER INFORMATION: Description of Artificial Sequence: Synthetic
      primer
```

-continued

```
<400> SEQUENCE: 1
agcaacaagu uuaguucguu cgagccgugc ga                                   32

<210> SEQ ID NO 2
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tgcatgcatg catcgcacgg ctcgaacgaa ctaaacttgt tgca                      44

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (44)
<223> OTHER INFORMATION: inverted dA

<400> SEQUENCE: 3
tgcatgcatg catcgcacgg ctcgaacgaa ctaaacttgt tgca                      44
```

SEQUENCING AND GENOTYPING USING REVERSIBLY TERMINATING NUCLEOTIDES

CROSS-REFERENCE TO RELATED APPLICATIONS

This application claims the benefit of U.S. Provisional Application No. 60/752,827, filed Dec. 21, 2005, and 60/844,041, filed Sep. 11, 2006, the disclosures of which are both incorporated by reference in their entirety for all purposes.

REFERENCE TO SEQUENCE LISTING

This application contains a Sequence Listing submitted as an electronic text file named "23360_US2_Seq_List", having a size in bytes of 1.15 kb, and created on May 8, 2008. The information contained in this electronic file is hereby incorporated by reference in its entirety pursuant to 37 CFR §1.52 (e)(5).

BACKGROUND OF THE INVENTION

DNA sequence analysis techniques have evolved to efficiently handle large scale sequencing projects. However, there are limitations in the currently available techniques when applied to high throughput sequencing projects where it is desirable to limit costs and retain sufficient speed. For example, classic Sanger dideoxy sequencing methods employ a step of resolving DNA fragments on a gel. This step does not lend itself to very large-scale multiplexing or parallel processing and further, has the problem of band compression during electrophoresis. Other techniques have been developed to increase the speed and decrease the cost of sequencing. These include sequencing by hybridization (see, e.g., Bains and Smith, *J. Theoret. Biol.* 135:303-307, 1988; Drmanac et al. *Genomics* 4:114-128, 1989; Khrapko et al. *FEBS Lett.* 256:118-122, 1989; Southern, WO10977, 1989); parallel signature sequencing based on ligation and cleavage (e.g., Brenner et al. *Proc. Natl. Acad. Sci.* 97:1665-1670, 2000); sequencing using reversible chain terminating nucleotides (see, e.g., U.S. Pat. Nos. 5,902,723 and 5,547,83; Canard and Arzumanov, *Gene* 11:1 (1994); and Dyatkina Arzumanov, *Nucleic Acids Symp Ser* 18:117 (1987)); reversible chain termination with DNA ligase (see, e.g., U.S. Pat. No. 5,403,708); time resolved sequencing (see, e.g., Johnson et al., *Anal. Biochem.* 136:192 (1984); and pyrosequencing (e.g., Ronaghi et al. *Anal. Biochem* 242:84-89, 1996).

Pyrosequencing is based on the concept of sequencing by synthesis (e.g., U.S. Pat. No. 4,863,849). The technique can be applied to massively parallel sequencing projects. For example, using an automated platform, it is possible to carry out hundreds of thousands of sequencing reactions simultaneously. Sequencing by synthesis differs from the classic dideoxy sequencing approach in that instead of generating a large number of sequences simultaneously and then characterizing them at a later step, real time monitoring of the incorporation of each base into a growing chain is employed. Although this approach is slow in the context of an individual sequencing reaction, it can be used for generating large amounts of sequence information in each cycle when hundreds of thousands to millions of reactions are performed in parallel. Despite these advantages, there are still limitations in the pyrosequencing approach. For example, there are difficulties in determining the number of incorporated nucleotides in homopolymeric regions, due to the nonlinear signal response following the incorporation of multiple identical molecules. Other Sequencing by Synthesis approaches on solid phase arrays that do not employ reversible terminators have similar disadvantages.

A method of sequencing using chemically reversible terminators using 3'-O-Allyl modified nucleotide analogs has recently been described (Ruparel et al., *Proc. Natl. Acad. Sci.* 102:5932-5937, 2005). In this method, the nucleotide analog contains an allyl moiety that caps the 3'-OH group and a fluorophore linked to the 5' position of the uracil through a photocleavable linker. This nucleotide is a substrate for a DNA polymerase. After incorporation into a DNA strand and photocleavage of the linker, the allyl group is removed using a Pd-catalyzed reaction, and the polymerase reaction is reinitiated. Thus, these analogs can act as reversible terminators in sequencing by synthesis reactions. Other reversible terminators are described, e.g., in U.S. Pat. Nos. 5,872,244; 6,232,465; 6,214,987; 5,808,045; 5,763,594, and 5,302,509; and U.S. Patent Application Publication No. 20030215862. The blocked 3'-OH type of reversible terminators suffer from several drawbacks including poor incorporation and deblocking efficiencies and the tedious conditions used for deblocking. A highly desirable method for high throughput sequencing based on reversible terminators demonstrates near perfect incorporation, chain termination, and deblocking efficiencies in order to minimize problems and background signals from out of phase reactions.

Recently, 2'-modified (e.g., 2'-phosphate) nucleoside 5' triphosphates have been described that can be used as substrates for certain nucleic acid polymerizing enzymes for only a single base incorporation (see, e.g., US Patent Application Publication Nos. 2005/00373898 and 2005/0037991). The present invention provides new methods of sequencing and genotyping that use 2'-terminator nucleotides in a reversible termination sequencing reaction.

BRIEF SUMMARY OF THE INVENTION

This invention provides, for example, a method of determining a nucleic acid sequence using a 2'-modified nucleotide that serves as a reversible terminator. In certain embodiments, incorporation of the 2'-modified reversible terminator nucleotide into a nucleic acid chain that is being elongated results in a detectable signal. Exemplary methods of detecting the detectable signal include, e.g., detecting released pyrophosphate by coupled enzyme cascades resulting in a luminescent signal, detecting a fluorescent label on the incorporated nucleotide (cleavable, for multiple additions), detecting a terminal-phosphate labeled nucleoside, detecting via a polyphosphate/phosphatase strategy, among other approaches. Treatment of the incorporated nucleotide with an activity to remove the modification or blocking group provides for further extension of the nucleic acid chain. The invention additionally includes, e.g., kits comprising components for determining a sequence, e.g., for sequencing, genotyping, and the like, using a reversible termination method of the invention; and systems for performing such a sequence analysis.

In one aspect, the invention provides a method of sequencing at least a portion of a template nucleic acid, the method comprising:

(a) incubating at least one template nucleic acid with at least one polymerase, at least one 2'-modified reversible terminator nucleotide (e.g., a 2'-monophosphate-3'-hydroxyl nucleotide, etc.), and at least one primer nucleic acid that is complementary to at least a subsequence of the template nucleic acid, whereby the polymerase extends the primer nucleic acid to produce at least one primer extension product that incorporates the 2'-modified reversible terminator nucleotide at a 3'-terminal end of the primer extension product;

(b) removing a blocking group (e.g., a phosphate or the like) from a 2' position of the 2'-modified reversible terminator nucleotide at the 3'-terminal end of the primer extension product; and, (c) identifying the 2'-modified reversible terminator nucleotide in the primer extension product prior to and/or during (b), whereby at least a portion of a base sequence of the template nucleic acid is determinable from the identified 2'-modified reversible terminator nucleotide, thereby sequencing at least the portion of the template nucleic acid. In certain embodiments, (b) comprises incubating the primer extension product with an activity that removes the blocking group (e.g., a phosphate, etc.) at the 2' position. The method typically includes repeating (a)-(c) one or more times.

In some embodiments, the modification at the 2' position is a phosphate or a modified phosphate, which can be removed, e.g., enzymatically using an enzyme such as, a phosphatase, an exonuclease III, an endonuclease IV, a polynucleotide kinase, a phosphodiesterase, or a combination of a phosphodiesterase and a phosphatase. In certain embodiments where phosphodiesterase enzymes, such as snake venom diesterases, are used, terminator nucleotides are modified to contain, e.g., an alpha-phosphorothioate modification.

In typical embodiments, the 2' modified reversible terminator nucleotide is selected from the group consisting of the structures shown in FIG. 1A-1H.

In certain embodiments, the 2'-modified reversible terminator nucleotide is labeled with at least one labeling moiety, such as a fluorescent dye, a luminescent molecule, or a radioisotope. In some embodiments, the labeling moiety can be attached to the 2'-modified reversible terminator nucleotide at the base via a cleavable linker, and the method further comprises a step of cleaving the linker. The labeling can be attached at various positions, such as at a sugar residue of the 2'-modified reversible terminator nucleotide or a phosphate present at the 2' modification position, or the terminal phosphate on the polyphosphate portion. In some embodiments, the 2'-modified reversible terminator nucleotides used in the methods described herein are unlabeled.

In some embodiments, the 2'-modified reversible terminator nucleotide is linked to two labeling moieties that comprise a donor and an acceptor, such as a fluorescent reporter and quencher pair. In particular embodiments, the donor and acceptor are capable of undergoing fluorescence resonance energy transfer.

The invention includes embodiments in which the quencher moiety is linked to the base of the 2'-modified reversible terminator nucleotide and the reporter moiety is linked to a phosphate, with the proviso that the phosphate is not the alpha phosphate of the 2'-modified reversible terminator nucleotide. For example, the phosphate can be a terminal delta or gamma phosphate on the polyphosphate portion, a beta phosphate, or a phosphate present at the 2' position of the 2'-reversible terminator nucleotide.

In certain embodiments, one labeling moiety is linked to a phosphate present at the 2' position of the 2'-modified reversible terminator nucleotide and the second labeling moiety is linked to a second phosphate, e.g., a gamma phosphate or the like. In some embodiments, these labeling moieties include, e.g., reporter and quencher moieties.

The methods of the invention include embodiments where the reaction mixture comprises four different 2'-modified reversible terminator nucleotides, each having a different base and labeled with a different labeling moiety, such that a different signal is generated for each nucleotide. In certain embodiments, the 2'-modified reversible terminator nucleotides utilized in the methods described herein are not labeled. Alternative embodiments include a detecting step that comprises detecting pyrophosphate generated upon incorporation of the 2'-modified reversible terminator nucleotide.

In another aspect, the invention includes a kit for determining a sequence, e.g., for re-sequencing, de novo sequencing, genotyping and the like, comprising: at least one 2'-modified reversible terminator nucleotide, and a reagent for removing the modification at the 2' position of the 2'-modified reversible terminator nucleotide. To illustrate, the kit can have a reagent that is selected from the group consisting of a phosphatase, an exonuclease, a phosphodiesterase, an endonuclease IV, and a polynucleotide kinase. Such a kit can further comprise a polymerase.

In some embodiments, the 2'-modified reversible terminator nucleotide included in the kit is attached to a label. The kit can optionally include at least one extendable nucleotide.

The invention also provides a method of genotyping, comprising:

a) incubating a template nucleic acid in a reaction mixture comprising a primer, a polymerase and a 2'-modified reversible terminator nucleotide, said modified reversible terminator nucleotide comprising one of the four naturally occurring bases or analogs thereof and further comprising a modification at the 2' position that terminates synthesis under conditions in which the primer anneals to the template nucleic acid and is extended by the polymerase present in the reaction to form an extended product;

b) determining if a signal indicative of incorporation of the 2'-modified reversible terminator nucleotide into the extended product is present;

c) if said signal is not present, repeating steps a) and b) with a different 2'-modified reversible terminator nucleotide, said different 2'-modified reversible terminator nucleotide comprising a different one of the four naturally occurring bases or analogs thereof, d) incubating the extended product with an activity that removes the modification at the 2' position present on the reversible terminator nucleotide, e) repeating steps a) to d) a desired number of times to determine the sequence of a portion of said template nucleic acid, and f) comparing the sequence of the portion of the template nucleic acid to a known sequence of a polymorphic site.

In an additional aspect, the invention provides a system for sequencing a nucleic acid, comprising:

a thermal cycler, comprising a reaction chamber wherein a template nucleic acid is incubated in a reaction mixture comprising a primer, a polymerase and a 2'-modified reversible terminator nucleotide, said modified reversible terminator nucleotide comprising one of the four naturally occurring bases or analogs thereof and further comprising a modification at the 2' position that terminates synthesis, the thermal cycler being effective to create conditions in which the primer anneals to the template nucleic acid and is extended by the polymerase present in the reaction to form an extended product;

said reaction chamber having an inlet port and an outlet port for adding and removing reagents; and a detector, the detector being effective to detect a signal indicative of incorporation of the 2'-modified reversible terminator nucleotide into the extended product.

In a further aspect, the invention provides a labeled 2'-modified reversible terminator nucleotide selected from the group consisting of:

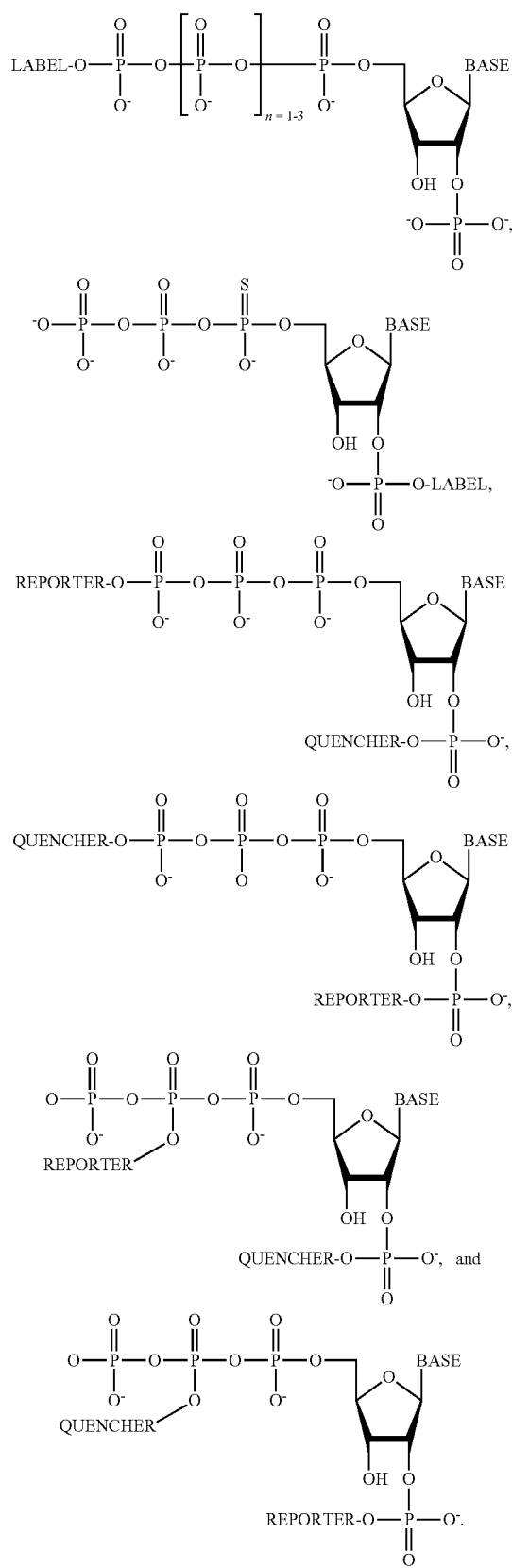

In certain embodiments, the 2'-modified reversible terminator nucleotides referred to herein are unlabeled.

The invention also provides a method of sequencing at least a portion of a template nucleic acid, comprising:

a) incubating the template nucleic acid in a reaction mixture comprising a primer, a polymerase, and a 2'-modified reversible terminator nucleotide, under conditions in which the primer anneals to the template nucleic acid and is extended by the polymerase present in the reaction to form an extended product;

b) determining the presence of a signal indicative of incorporation of the 2'-modified reversible terminator nucleotide into the extended product;

c) incubating the extended product with an activity that removes the modification at the 2' position present on the reversible terminator nucleotide;

d) repeating steps a) to c) a desired number of times to determine the sequence of at least portion of the template nucleic acid.

In some embodiment, step (a) is carried out using a plurality of different 2'-modified reversible terminator nucleotides in a single reaction mixture, each different 2'-modified reversible terminator nucleotide comprising a different base. For example, each different 2'-modified reversible terminator nucleotide can be added sequentially until a signal indicative of incorporation of the 2'-modified reversible terminator nucleotide into the extended product is detected. Alternatively, each different 2'-modified reversible terminator nucleotide can be added simultaneously in embodiment in which different 2'-modified reversible terminator nucleotides are labeled with a different labeling moiety.

In another aspect, the invention provides a method of sequencing at least a portion of a template nucleic acid, comprising:

a) incubating the template nucleic acid in a reaction mixture comprising a primer, a polymerase, and a 2'-modified reversible terminator nucleotide, the modified reversible terminator nucleotide comprising one of the four naturally occurring bases or analogs thereof and further comprising a modification at the 2' position that terminates synthesis, under conditions in which the primer anneals to the template nucleic acid and is extended by the polymerase present in the reaction to form an extended product;

b) determining if a signal indicative of incorporation of the 2'-modified reversible terminator nucleotide into the extended product is present;

c) if the signal is not present, repeating steps a) and b) with a different 2'-modified reversible terminator nucleotide, said different 2'-modified reversible terminator nucleotide comprising a different one of the four naturally occurring bases or analogs thereof, d) incubating the extended product with an activity that removes the modification at the 2' position present on the reversible terminator nucleotide, and e) repeating steps a) to d) a desired number of times to determine the sequence of at least a portion of the template nucleic acid.

BRIEF DESCRIPTION OF THE DRAWINGS

FIGS. 1A-1H show exemplary 2'-modified reversible terminators.

DETAILED DESCRIPTION OF THE INVENTION

Figure 1D:
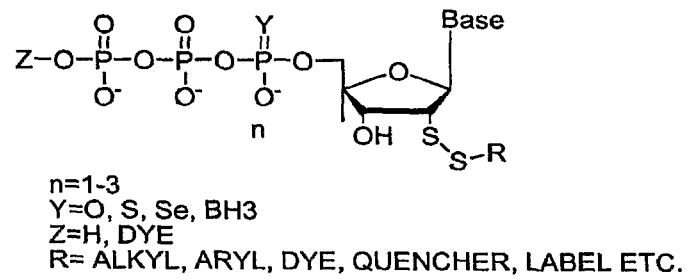
Figure 1E:
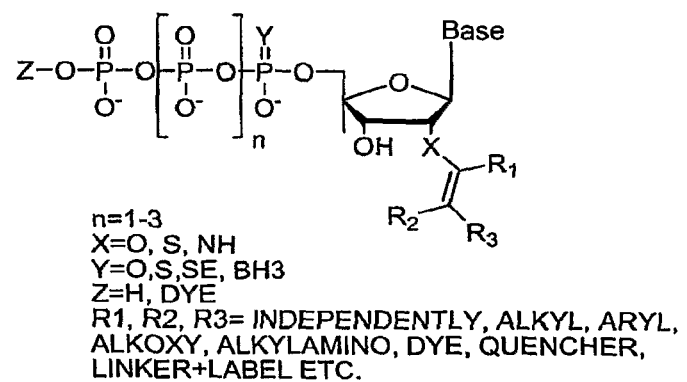
Figure 1F:
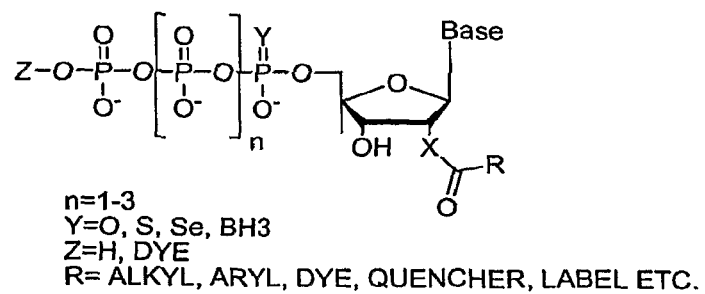
Figure 1G:
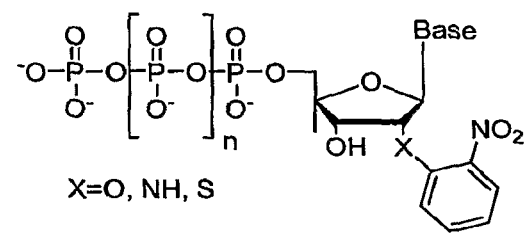
Figure 1H:
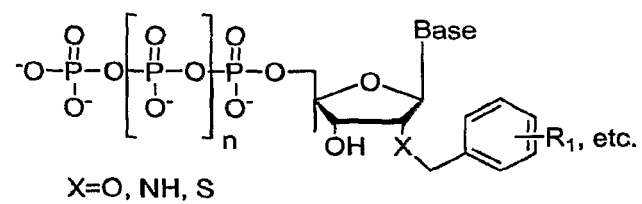

This invention provides, e.g., a method of performing sequencing employing modified nucleotides that have a modification at the 2' OH position that can terminate extension of a nucleic acid chain. The modification at the 2' OH position is then typically removed in a subsequent step, rendering the newly added nucleotide extendable, in order to allow further chain extension. Incorporation of the modified 2'-terminator nucleotide ultimately results in a detectable signal, either directly or indirectly. The detectable signal can be generated at the time the terminator is incorporated or when the modification is removed. The method can be used, e.g., for high throughput sequencing methods to determine the sequence of a desired nucleic acid and for applications such as genotyping.

DEFINITIONS

The term "2'-modified reversible terminator nucleotide" (also sometimes called a "2'-modified reversible terminator") refers to a nucleotide analog that comprises a removable blocking group at the 2'-position of the sugar moiety of the nucleotide. A "removable blocking group" refers to a chemical group or moiety that at least partially terminates the extension of a nucleic acid after incorporation of the 2'-modified reversible terminator nucleotide, but that can be removed so that extension of the nucleic acid molecule can be restored. The nature of the blocking group is not critical to the invention so long as the presence of the blocking group terminates extension, but extension is restored after cleavage of the blocking group. An exemplary removable blocking group is a phosphate group. Other representative blocking groups are also described herein. Exemplary 2'-terminator nucleotides include 2'-monophosphate-3'-hydroxyl-5'-triphosphate nucleosides and 2'-monophosphate-3'-hydroxyl-5'-diphosphate nucleosides. 2'-terminator nucleotides for use in this invention are described, e.g., in U.S. Patent Application Publication Nos. 20050037991 and 20050037398.

The particular means for removing the blocking group will, of course, depend upon the removable blocking group and is also not critical to the invention. Typically, the removable blocking group is removed by enzymatic, chemical or photochemical means.

The term "nucleic acid" refers to nucleotides (e.g., ribonucleotides, deoxyribonucleotides, 2'-terminator nucleotides, dideoxynucleotides, etc.) and polymers (e.g., comprising deoxyribonucleic acids (DNAs), ribonucleic acids (RNAs), DNA-RNA hybrids, oligonucleotides, polynucleotides, genes, cDNAs, aptamers, antisense nucleic acids, interfering RNAs (RNAi), molecular beacons, nucleic acid probes, peptide nucleic acids (PNAs), PNA-DNA conjugates, PNA-RNA conjugates, etc.) that comprise such nucleotides covalently linked together, either in a linear or branched fashion. A nucleic acid is typically single-stranded or double-stranded and will generally contain phosphodiester bonds, although in some cases, as outlined herein, nucleic acid analogs are included that may have alternate backbones, including, for example and without limitation, phosphoramide (Beaucage et al. (1993) Tetrahedron 49(10): 1925) and references therein; Letsinger (1970) J. Org. Chem. 35:3800; Sprinzl et al. (1977) Eur. J. Biochem. 81:579; Letsinger et al. (1986) Nucl. Acids Res. 14:3487; Sawai et al. (1984) Chem. Lett. 805; Letsinger et al. (1988) J. Am. Chem. Soc. 110: 4470; and Pauwels et al. (1986) Chemica Scripta 26: 1419), phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), methyl phosphonate linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895; Meier et al. (1992) Chem. Int. Ed. Engl. 31:1008; Nielsen (1993) Nature 365:566; Carlsson et al. (1996) Nature 380:207), which references are each incorporated by reference. Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863; Angew (1991) Chem. Intl. Ed. English 30: 423; Letsinger et al. (1988) J. Am. Chem. Soc. 110:4470; Letsinger et al. (1994) Nucleoside & Nucleotide 13:1597; Chapters 2 and 3, ASC Symposium Series 580, "Carbohydrate Modifications in Antisense Research", Ed. Y. S. Sanghvi and P. Dan Cook; Mesmaeker et al. (1994) Bioorganic & Medicinal Chem. Lett. 4: 395; Jeffs et al. (1994) J. Biomolecular NMR 34:17; Tetrahedron Lett. 37:743 (1996)) and non-ribose backbones, including those described in U.S. Pat. Nos. 5,235,033 and 5,034,506, and Chapters 6 and 7, ASC Symposium Series 580, Carbohydrate Modifications in Antisense Research, Ed. Y. S. Sanghvi and P. Dan Cook, which references are each incorporated by reference. Nucleic acids containing one or more carbocyclic sugars are also included within the definition of nucleic acids (see Jenkins et al. (1995) Chem. Soc. Rev. pp 169-176, which is incorporated by reference). Several nucleic acid analogs are also described in, e.g., Rawls, C & E News Jun. 2, 1997 page 35, which is incorporated by reference.

In addition to these naturally occurring heterocyclic bases that are typically found in nucleic acids (e.g., adenine, guanine, thymine, cytosine, and uracil), nucleic acid analogs also include those having non-naturally occurring heterocyclic bases, many of which are described, or otherwise referred to, herein. In particular, many non-naturally occurring bases are described further in, e.g., Seela et al. (1991) Helv. Chim. Acta 74:1790, Grein et al. (1994) Bioorg. Med. Chem. Lett. 4:971-976, and Seela et al. (1999) Helv. Chim. Acta 82:1640, which are each incorporated by reference. To further illustrate, certain bases used in nucleotides that act as melting temperature ($T_m$) modifiers are optionally included. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dc, etc.), and the like. See, e.g., U.S. Pat. No. 5,990,303, entitled "SYNTHESIS OF 7-DEAZA-2'-DEOXYGUANOSINE NUCLEOTIDES," which issued Nov. 23, 1999 to Seela, which is incorporated by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytosine; 5-fluorocytosine; 5-chlorocytosine; 5-iodocytosine; 5-bromocytosine; 5-methylcytosine; 5-propynylcytosine; 5-bromovinyluracil; 5 fluorouracil; 5-chlorouracil; 5-iodouracil; 5-bromouracil; 5-trifluoromethyluracil; 5-methoxymethyluracil; 5-ethynyluracil; 5-propynyluracil, and the like. In certain instances the term "Base" is meant to encompass protected bases where the exocyclic amines are modified with protecting groups.

A "nucleoside" refers to a nucleic acid component that comprises a base or basic group (e.g., comprising at least one homocyclic ring, at least one heterocyclic ring, at least one aryl group, and/or the like) covalently linked to a sugar moiety (e.g. a ribose sugar, etc.), a derivative of a sugar moiety, or a functional equivalent of a sugar moiety (e.g., an analog, such as a carbocyclic ring). For example, when a nucleoside includes a sugar moiety, the base is typically linked to a 1'-position of that sugar moiety. As described above, a base can be naturally occurring (e.g., a purine base, such as adenine (A) or guanine (G), a pyrimidine base, such as thymine (T), cytosine (C), or uracil (U)), or non-naturally occurring (e.g., a 7-deazapurine base, a pyrazolo[3,4-d]pyrimidine base, a propynyl-dN base, etc.). Exemplary nucleosides include ribonucleosides, deoxyribonucleosides, dideoxyribonucleosides, carbocyclic nucleosides, etc.

A "nucleotide" refers to an ester of a nucleoside, e.g., a phosphate ester of a nucleoside. For example, a nucleotide can include 1, 2, 3, or more phosphate groups covalently linked to a 5' position of a sugar moiety of the nucleoside (e.g., nucleoside polyphosphates).

An "oligonucleotide" refers to a nucleic acid that includes at least two nucleotides, typically more than three nucleotides, and more typically greater than ten nucleotides. The exact size of an oligonucleotide generally depends on various factors, including the ultimate function or use of the oligonucleotide. Oligonucleotides are optionally prepared by any suitable method, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979). Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103: 3185-3191; automated synthesis methods; or the solid support method of U.S. Pat. No. 4,458,066, among other methods known in the art, which references are each incorporated by reference.

A "primer" is typically a nucleic acid that can hybridize to a template nucleic acid and permit chain extension or elongation using, e.g., a nucleotide incorporating biocatalyst, such as a thermostable polymerase under appropriate reaction conditions. A primer nucleic acid is typically a natural or synthetic oligonucleotide (e.g., a single-stranded oligodeoxyribonucleotide, etc.). Although other primer nucleic acid lengths are optionally utilized, they typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. A primer nucleic acid can be labeled, if desired, by incorporating a label detectable by, e.g., spectroscopic, photochemical, biochemical, immunochemical, or chemical techniques. To illustrate, useful labels include radioisotopes, fluorescent dyes, electron-dense reagents, enzymes (as commonly used in ELISAs), biotin, or haptens and proteins for which antisera or monoclonal antibodies are available. Many of these and other labels are described further herein and/or are otherwise known in the art. In addition, a primer nucleic acid can simply provide a substrate for a nucleotide incorporating biocatalyst in a template independent manner.

A "template nucleic acid" refers to a nucleic acid to which a primer nucleic acid can hybridize and be extended. Accordingly, template nucleic acids include subsequences that are at least partially complementary to the primer nucleic acids. Template nucleic acids can be derived from essentially any source. To illustrate, template nucleic acids are optionally derived or isolated from, e.g., cultured microorganisms, uncultured microorganisms, complex biological mixtures, tissues, sera, pooled sera or tissues, multispecies consortia, ancient, fossilized or other nonliving biological remains, environmental isolates, soils, groundwaters, waste facilities, deep-sea environments, or the like. Further, template nucleic acids optionally include or are derived from, e.g., individual cDNA molecules, cloned sets of cDNAs, cDNA libraries, extracted RNAs, natural RNAs, in vitro transcribed RNAs, characterized or uncharacterized genomic DNAs, cloned genomic DNAs, genomic DNA libraries, enzymatically fragmented DNAs or RNAs, chemically fragmented DNAs or RNAs, physically fragmented DNAs or RNAs, or the like. Template nucleic acids can also be chemically synthesized using techniques known in the art. In addition, template nucleic acids optionally correspond to at least a portion of a gene or are complementary thereto. As used herein, a "gene" refers to any segment of DNA associated with a biological function. Thus, genes include coding sequences and optionally, the regulatory sequences required for their expression. Genes also optionally include non-expressed DNA segments that, for example, form recognition sequences for other proteins.

An "extendable nucleotide" refers to a nucleotide to which at least one other nucleotide can be added or covalently bonded, e.g., in a reaction catalyzed by a nucleotide incorporating biocatalyst once the extendable nucleotide is incorporated into a nucleotide polymer. Examples of extendable nucleotides include deoxyribonucleotides and ribonucleotides, and derivatives thereof bearing, e.g., labels. An extendable nucleotide is typically extended by adding another nucleotide at a 3'-position of the sugar moiety of the extendable nucleotide.

A "non-extendable" or "terminator" nucleotide refers to a nucleotide, which upon incorporation into a nucleic acid prevents, or substantially reduces the rate of, further extension of the nucleic acid, e.g., by at least one nucleotide incorporating biocatalyst.

A "tetraphosphate nucleotide" refers to a nucleotide that includes four phosphate groups. Exemplary tetraphosphate nucleotides include 2'-monophosphate-5'-triphosphate nucleosides and 3'-monophosphate-5'-triphosphate nucleosides.

A "negatively charged blocking group" refers to a blocking group that comprises at least one negative charge, which negative charge at least contributes to the non-extendable property of the nucleotide to which it is attached, e.g., by electrostatic repulsion of incoming nucleotides. To illustrate, negatively charged blocking groups at the 2'-positions of nucleotides of the invention optionally include phosphate, carboxy, or other groups referred to herein that typically comprise at least one negative charge upon ionization in a physiological pH range. In certain embodiments, multiple factors can contribute to the non-extendable property of a nucleotide of the invention including, e.g., blocking group charge and size.

A "full-length sequence" refers to a nucleic acid sequence that comprises at least substantially the same number of nucleotides as a reference sequence or a nucleic acid sequence that is at least partially complementary to the reference sequence. In certain embodiments of the invention, for example, an extended primer nucleic acid is complementary to a full-length sequence of a template nucleic acid or other reference sequence.

A "subsequence" or "fragment" refers to a portion of a nucleic acid sequence where the subsequence or fragment comprises contiguous nucleotides of the sequence.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

The term "attached" or "linked" refers to interactions including, but not limited to, covalent bonding, ionic bonding, chemisorption, physisorption, and combinations thereof.

A "linker" or "spacer" refers to a chemical moiety that covalently or non-covalently (e.g., ionically, etc.) attaches a compound or substituent group to, e.g., a solid support, another compound or group, or the like. For example, a linker optionally attaches a label (e.g., a fluorescent dye, a radioisotope, etc.) to a 2'-terminator nucleotide or the like. Linkers are typically bifunctional chemical moieties and in certain embodiments, they comprise cleavable attachments, which can be cleaved by, e.g., heat, an enzyme, a chemical agent, electromagnetic radiation, etc. to release materials or compounds from, e.g., a solid support, another compound, etc. A careful choice of linker allows cleavage to be performed under appropriate conditions compatible with the stability of the compound and assay method. Generally a linker has no specific biological activity other than to, e.g., join chemical species together or to preserve some minimum distance or other spatial relationship between such species. However, the constituents of a linker may be selected to influence some property of the linked chemical species such as three-dimensional conformation, net charge, hydrophobicity, etc. Additional description of linker molecules is provided in, e.g., Lyttle et al. (1996) *Nucleic Acids Res.* 24(14):2793, Shchepino et al. (2001) Nucleosides, Nucieotides, & Nucleic Acids 20:369, Doronina et al (2001) Nucleosides, Nucleotides, & Nucleic Acids 20:1007, Trawick et al. (2001) Bioconjugate Chem. 12:900, Olejnik et al. (1998) Methods in Enzymology 291:135, Pljevaljcic et al. (2003) J. Am. Chem. Soc. 125(12): 3486, Ward, et. al., U.S. Pat. No. 4,711,955, Stavrianopoulos, U.S. Pat. No. 4,707,352, and Stavrianopoulos, U.S. Pat. No. 4,707,440, which are each incorporated by reference.

A "label" refers to a moiety attached (covalently or non-covalently), or capable of being attached, to a molecule, which moiety provides or is capable of providing information about the molecule (e.g., descriptive, identifying, etc. information about the molecule). Exemplary labels include fluorescent labels, weakly fluorescent labels, non-fluorescent labels, colorimetric labels, chemiluminescent labels, bioluminescent labels, radioactive labels, mass-modifying groups, antibodies, antigens, biotin, haptens, and enzymes (including, e.g., peroxidase, phosphatase, etc.). To further illustrate, labels also include reporter and quencher moieties.

A "solid support" refers to a solid material which can be derivatized with, or otherwise attached to, a chemical moiety, such as a primer nucleic acid, a template nucleic acid, or the like. Exemplary solid supports include a plate, a bead, a microbead, a fiber, a whisker, a comb, a hybridization chip, a membrane, a single crystal, a ceramic layer, a self-assembling monolayer, and the like.

The phrase "in solution" refers to a reaction condition in which at least the reactants are not attached to a solid support. For example, certain extension reactions of the invention include incubating template nucleic acids, primer nucleic acids, 2'-terminator nucleotides, extendable nucleotides, and nucleotide incorporating biocatalysts together in solution.

The term "cleavage" refers to a process of releasing a material or compound from another compound or material or from a solid support, e.g., to permit analysis of the compound by solution-phase methods. See, e.g., Wells et al. (1998) "Cleavage and Analysis of Material from Single Resin Beads," J. Org. Chem. 63:6430-6431, which is incorporated by reference.

INTRODUCTION

This invention provides, e.g., a method of determining a nucleic acid sequence using a 2'-modified nucleotide that serves as a reversible terminator. In certain embodiments, incorporation of the 2'-modified reversible terminator nucleotide into a nucleic acid chain that is being elongated results in a detectable signal. In some exemplary embodiments, detectable signals are produced subsequent to incorporation of the 2'-modified reversible terminator nucleotide, e.g., when the modification is removed from the 2' position. Moreover, treatment of the incorporated nucleotide with an activity to remove the modification provides for the possibility of further extension of the nucleic acid chain.

2'-Modified Reversible Terminator Nucleotides

Certain 2'-modified terminator nucleotides are known in the art. Such nucleotides are described, for example, in U.S. Patent Application Publication Nos. 20050037991 and 20050037398. The terminator nucleotides can have naturally occurring bases, or analogs of those bases. Further, the term encompasses nucleotide analogs such as 5'-triphosphate, 5'-tetraphosphate and 5'-pentaphosphate analogs.

The modified nucleotides of this invention have a modification at the 2' sugar position, referred to herein as a blocking group, which inhibits extension of a nucleotide strand. The modification at the 2' sugar position in the terminator nucleotides can be any number of blocking groups, e.g., a negatively charged blocking group, a bulky blocking group and the like, that are incorporated at the 2' position of the sugar moiety. The blocking group of the terminator nucleotides used in this invention is removable, thus the terminators are reversible terminators. The blocking group can be removed by enzymatic, chemical, or other means.

The blocking group can be removed by, e.g., enzymatic, chemical, or photochemical means. Exemplary cleavable linkages include linkers that can be cleaved by enzymes, light, reducing agents, oxidizing agents, hydrating agents and the like.

In some embodiments, the 2' modification is a phosphate. Accordingly, the 2' modification is readily removed using an activity that removes phosphates. Often the activity is an enzymatic activity, e.g., a phosphatase, an exonuclease III, an endonuclease IV, or a polynucleotide kinase. In some instances, e.g., where a label is attached to the 2'-phosphate, phosphodiesterases, either alone or in combination with a phosphatase can be used to remove the phosphate group. This may be done with incorporation of phosphorothioate linkages to prevent degradation of the nucleic acid backbone.

In other embodiments, as also referred to above, the blocking group is attached to the 2' position via a linkage that can be cleaved enzymatically, chemically (e.g., reducing agents, oxidizing agents, hydrating agents, and the like) or via a photocleavable linkage. Photocleavable moieties, that can be used include 2-nitrobenzyl moieties, alpha-substituted 2-nitrobenzyl moieties (e.g., 1-(2-nitrophenyl)ethyl moieties), 3,5-dimethoxybenzyl moieties, thiohydroxamic acid, 7-nitroindoline moieties, 9-phenylxanthyl moieties, benzoin moieties, hydroxyphenacyl moieties, NHS-ASA moieties, and the like. Photocleavable linkers are described further in, e.g., U.S. Pat. Publication No. 2003/0099972.

Chemically cleavable linkers may also be used to attach the blocking group to the 2' position. Cleaving agents include chemical agents such as reducing agents that cleave disulfide bonds present in linkers. Any chemical modifications that are reversible under such conditions that are not detrimental to the nucleic acid can be used. Thus chemical modifications that can be readily reversed using mild acid or base, reducing agents, mild oxidizers, heat, catalysts, etc. are appropriate. For example, with appropriate substitutions, esters, allyl ethers, trityl ethers, benzyl ethers, can all act as chemically reversible modifiers.

In some embodiments, the blocking group is selected from one of those shown in FIG. 1. These blocking groups can be removed using known techniques. For example, the blocking groups shown in FIG. 1A can be removed, e.g., enzymatically, or with mild acid or heat when X=NH. The blocking groups exemplified in FIG. 1B can be removed, e.g., with fluoride ion treatment. Blocking groups as exemplified in FIG. 1C, such as a trityl or substituted trityl, can be removed, e.g., with mild acid or heat. The exemplary modifications shown in FIG. 1D can be removed, e.g., by disulfide cleavage using reducing agents. The 2' modifications shown in FIG. 1E can be removed, e.g., using palladium (see, e.g., Turro et al). The 2' blocking groups exemplified in FIG. 1F can be removed using agents such as esterases, proteases, and mild acid or base treatment, and the like. 2' modifications such as those shown in FIG. 1G can be removed, e.g., photochemically. Blocking groups such as those represented in FIG. 1H can be removed, e.g., by catalytic reduction.

The 2'-modified terminator nucleotides are typically synthesized using known techniques. Exemplary synthesis protocols are provided, e.g., in U.S. Patent Publication No. 20050037991.

Labels

Labeling Moieties

In some embodiments, 2'-modified terminator nucleotides of the invention comprise a label or components of a labeling system to allow detection of the incorporation of the nucleotide into a nucleic acid molecule. The signal can be generated based on a labeling strategy where the signal is detected upon incorporation of the nucleotide into the chain, or when the blocking group is removed from a 2'-modified nucleotide that has been appended to the nucleic acid chain. Such a label provides for generating a signal that indicates whether a nucleotide is incorporated into a nucleic acid chain. The concept of signal generation that is indicative of whether a nucleotide is incorporated includes either direct or indirect signaling and signal generation that occurs as the nucleotide is incorporated, e.g., removal of a gamma phosphate results in a signal, or a situation that involves an additional step after incorporation to detect the incorporated nucleotide, e.g., a step that removes the blocking group at the 2'OH group or embodiments employing photo- or chemical cleavage of a linker located on the base.

A 2'-modified terminator nucleotide can be labeled with any detectable label that generates a signal including, a radioactive label, a mass-modifying group, a fluorescent moiety, a luminescent moiety, an enzymatic moiety and the like. In typical embodiments, the label is a fluorescent label.

In the context of this invention, a label also refers to a labeling system in which multiple moieties, e.g., a pair of moieties, interact with one another to control signal generation. For example, these include donor/acceptor pairs in which a fluorescent emission from the donor results in excitation of the acceptor when the molecules are in close proximity. Accordingly, a signal generated by the donor and/or acceptor is different when the two molecules are separated from one another as compared to when they are in close proximity. A donor moiety, typically a fluorophore, absorbs energy at a first wavelength and emits at a second, longer wavelength. An acceptor refers to another moiety, such as a fluorophore, a chromophore, or a quencher that has an absorption spectrum that overlaps with the emission spectrum of the donor. Efficient energy transfer between the donor and acceptor depends, e.g., on the overlap between the donor emission and acceptor absorption spectra and the distance between the donor and acceptor.

Fluorescent moieties that can be used as labels are generally known to persons of skill in the art. These include fluorescein-family dyes (Integrated DNA Technologies, Inc., Coralville, Iowa), polyhalofluorescein-family dyes (ABI, Foster City, Calif.), hexachlorofluorescein-family dyes (ABI, Foster City, Calif.), coumarin-family dyes (Invitrogen-Molecular Probes, Inc., Eugene, Oreg.), rhodamine-family dyes (GE Healthcare), cyanine-family dyes, oxazine-family dyes, thiazine-family dyes, squaraine-family dyes, chelated lanthanide-family dyes, and BODIPY®-family dyes (Molecular Probes, Inc.). Other examples of fluorescent moieties can be found in U.S. Pat. Nos. 6,406,297; 6,221,604; 5,994,063; 5,808,044; 5,880,287; 5,556,959 and 5,135,717. Additional detectable labels that are optionally utilized include, e.g., dimethylacridinone (DDAO), 4-methylumbelliferone, 6,8-difluoro-4-methylumbelliferone, and the like. As referred to above, fluorescent moieties that can be used as labels are commercially available from, for example, Invitrogen-Molecular Probes (Eugene, Oreg.), among many others.

In some embodiments, the 2'-modified reversible terminator nucleotides are labeled with a fluorescent-quencher pair (e.g., a donor-acceptor pair). Quencher moieties include, e.g., fluorescein-family dyes, polyhalofluorescein-family dyes, hexachlorofluorescein-family dyes, coumarin-family dyes, rhodamine-family dyes, cyanine-family dyes, oxazine-family dyes, thiazine-family dyes, squaraine-family dyes, chelated lanthanide-family dyes, BODIPY®-family dyes, low-fluorescent quencher moieties and non-fluorescent quencher moieties. In certain embodiments, the non-fluorescent quencher moieties can be BHQ™-family dyes (including the quenchers described in WO 01/86001, BHQ-1, BHQ-2, BHQ-3) (BioSearch Technologies, Novato, Calif.), or Dabcyl (Integrated DNA Technologies, Inc.). Other examples of specific quencher moieties include, for example, TAMRA (N,N,N',N'-tetramethyl-6-carboxyrhodamine) (Invitrogen-Molecular Probes, Inc.), DABCYL (4 (4' dimethylaminophenylazo)benzoic acid), Iowa Black™ (Integrated DNA Technologies, Inc.), Cy3™, Cy3.5™, Cy5™, or Cy5.5™ (GE Healthcare), and the like.

Exemplary combinations of fluorescent moieties and quencher moieties that are used include, for example, a 6-carboxyfluorescein (FAM) fluorophore moiety and a Cy5™ quencher moiety; a fluorophore moiety selected from the group consisting of FAM, TET, JOE, HEX, Oregon Green and a BHQ-1 quencher moiety; a fluorophore moiety selected from the group consisting of FAM, TAMRA, ROX, Cy3, Cy3.5, CAL Red, Red 640 and a BHQ-2 quencher moiety; a fluorophore moiety selected from the group consisting of Cy5 and Cy5.5 and a BHQ-3 quencher moiety.

Site of Label Attachment

The label (or labeling components) can be attached at any suitable site that provides for detecting 2'-modified reversible terminator nucleotide that is incorporated into a nucleic acid chain. The attachment of the label to the nucleotide also provides for removing the signal, so that signal from the label that is incorporated into a nucleic acid strand can be removed. For example, in instances in which a single label is attached to the 2'-modified terminator nucleotide, the label can be attached at the base or sugar via a cleavable linker. Once the signal from the label incorporated into the extended nucleic acid chain has been detected, the label can be removed by cleavage of the linker. In other embodiments, the labeling moiety is attached to a phosphate present at the 2' modification position. The labeling moiety can then be removed, e.g., by a phosphodiesterase and/or phosphatase, when the 2'-modification is removed from the 2'-modified terminator nucleotide.

Where more than one component is involved in the labeling system, the components are attached to appropriate sites on the 2'-modified terminator nucleotide. For example, the labeling system may comprise a donor-acceptor pair, such as a fluorescent dye reporter molecule and a quencher. The examples discussed in this section use a fluorescent reporter and quencher as exemplary labeling components. It is understood in the art that similar labeling configurations can be used for other multi-component labeling systems.

In some embodiments, a 2'-modified reversible terminator nucleotide can have a quencher moiety that is linked to the base or the sugar and a reporter that is linked to a phosphate. Typically the phosphate is any phosphate on the nucleotide other than an alpha phosphate. Accordingly, the reporter can be positioned at the 2' position of the sugar attached to the 2'-phosphate modifying group. In other embodiments, the reporter is preferably linked to a gamma phosphate. The reporter can also be linked to a beta phosphate, and in embodiments where a tetraphosphate or pentaphosphate 2'-modified terminator nucleotide is used, the reporter may also be attached to one of the additional phosphates.

In certain applications, it may also be desirable to use alternative configurations. For example, a fluorescent reporter may be linked to a base of a 2'-modified terminator nucleotide by a cleavable linker and the quencher linked to a phosphate. Such a configuration may be useful, for example, where a sequencing reaction of the invention uses four 2'-modified terminator nucleotides, each labeled with a fluorescent reporter that is a different color. A quencher is present on the beta or gamma phosphate, accordingly, all four analogs are present, but yield little or no signal. Upon incorporation of one of the analogs into the nucleic acid strand, signal from the incorporated nucleotide can be detected. Following dye removal via cleaving the cleavable linker, the 2'-blocking group is removed.

In other embodiments, one labeling moiety, e.g., a fluorescent reporter or quencher, is linked to a phosphate present at the 2' position of the 2'-modified terminator nucleotide and a second labeling moiety, the corresponding reporter or quencher, depending on the identity of the first labeling moiety, is linked to a second phosphate other than the alpha phosphate, e.g., a gamma or a beta phosphate, or other phosphate positions in tetraphosphate or pentaphosphate 2-modified terminator nucleotides.

The labels can be linked to the 2'-modified terminator nucleotides using known techniques. Exemplary cleavable linkages include linkers that can be cleaved by light, reducing agents, oxidizing agents, hydrating agents and the like. Examples are described, e.g., in U.S. Patent Application Publication No. 20050037398.

Noncleavable linkers are also employed, for example, for linking a reporter to a gamma or beta phosphate, or other moiety, e.g., a blocking group on the modified nucleotide, that is removed during synthesis or once the modified nucleotide is incorporated into the nucleic acid strand. Such attachments use known techniques.

Guidance for attaching labels to nucleotides or other organic molecules is readily available in the art (see, e.g., Hermanson, Bioconjugate Techniques, (1996) Academic Press, San Diego, Calif. pp. 40-55, 643-71; Garman, 1997, Non-Radioactive Labelling: A Practical Approach, Academic Press, London.; Beaucage et al., Current Protocols in Nucleic Acid Chemistry, John Wiley & Sons, New York, N.Y. (2000); Handbook of Fluorescent Probes and Research Products, 9th ed., Molecular Probes, Inc., Eugene, Oreg. (2002); and Pierce Applications Handbook and Catalog 2003-2004, Pierce Biotechnology, Rockford, Ill. (2003).

Sequencing Reaction Employing 2'-Modified Terminator Nucleotides

Sequencing reactions employing 2'-modified reversible terminator nucleotides of this invention include a step of removing the 2'-modifying group to reverse termination of chain elongation. Thus, the invention provides for real-time monitoring of a nucleotide strand that is being elongated in an extension reaction. Such a sequencing reaction can be performed in various formats.

In one embodiment, all four nucleotides (which term encompasses analogs of the naturally occurring nucleotide dATP, dGTP, dCTP, and dTTP) are present as 2'-modified terminator nucleotides, each labeled with a distinguishable label. The incorporation of a particular nucleotide can be detected, for example, using a fluorescent reporter/quencher system. Once a nucleotide is incorporated, the signal can be removed. The blocking modification at the 2' position is also removed to provide for continued chain elongation.

In typical embodiments, sequencing steps are performed sequentially using one 2'-modified terminator nucleotide at a time. In this method, one 2'-modified terminator is included in a reaction mixture comprising the nucleic acid template, a suitable primer, a polymerase, and other reaction components. The reaction is carried out under conditions in which the primer hybridizes to the nucleic acid template and can be extended. Incorporation of the 2'-modified terminator is monitored. If the nucleotide is incorporated, a signal is detected and the 2'-modification is removed to permit continued elongation. In some embodiments, the signal is detected prior to or concurrent with the 2'-modification being removed. If the modified terminator is not incorporated, a second 2'-modified terminator (corresponding to a different base) is employed. The steps are repeated until incorporation of one of the four 2'-modified nucleotides is detected. After removal of the modifying group, the next position in the template nucleic acid is queried using the same sequential analysis.

In embodiments, in which the four nucleotides are sequentially added, the nucleotides may be labeled, either with the same, or different labels.

Incorporation of the 2'-modified terminator nucleotide can be detected by any of a number of methods. In some embodiments, incorporation of the nucleotide is determined via detecting pyrophosphate that is released upon incorporation of the nucleotide, as in pyrosequencing, Sequencing by synthesis using pyrosphophate-based detection has been described in U.S. Pat. No. 4,971,903 and Hyman, *Anal Biochem.* 174:423 (1988); Rosenthal, International Patent Application Publication 761107 (1989); Metzker et al., *Nucl. Acids Res.* 22:4259 (1994); Jones, *Biotechniques* 22:938 (1997); Ronaghi et al., *Anal. Biochem.* 242:84 (1996), Nyren et al., *Anal. Biochem.* 151:504 (1985). Detection of ATP sulfarylase activity is described, e.g., in Karamohamed and Nyren, *Anal. Biochem.* 271:81 (1999). These methods are based on the detection of the pyrophosphate (PPi) released during the DNA polymerase reaction. As nucleotriphosphates are added to a growing nucleic acid chain, PPi is released. This can be quantitatively measured by the conversion of PPi to ATP by the enzyme sulfurylase, and the subsequent production of visible light by firefly luciferase. Several assay systems based on this mechanism have been described (see, e.g. WO93/23564, WO 98/28440 and WO98/13523; and Ronaghi et al., Science 281:363 (1998)).

In other embodiments, incorporation can be detected, for example, by detecting the presence of any label, such as a fluorescence label. The detection method that is employed is selected in accordance with the label. Thus, the detection step can detect light emission, radioactivity, and the like.

In some embodiments, sequence analysis in accordance with the invention can be performed for various applications in which it is desirable to determine the sequence of one or more positions of a nucleic acid. These applications include resequencing, single nucleotide polymorphism (SNP) genotyping, molecular haplotyping, allelic frequency determination, methylation analysis and mixed genotype detection.

For example, genotyping can be performed in sequential steps by incubating a template nucleic acid in a reaction mixture comprising a primer, a polymerase and a 2'-modified terminator nucleotide. The primer is designed to target a particular region of a nucleic acid. The reaction is monitored to determine if a signal indicative of incorporation of the 2'-modified terminator is present. If it is not present, a subsequent step is performed using a different, i.e., having a different base, 2'-modified terminator nucleotide. Once a 2'-modified nucleotide is incorporated, the modification group is removed to allow for continued chain elongation.

It is understood that in some applications, it may not be necessary to query the template sequence using 2'-modified reversible terminator nucleotides corresponding to all four naturally occurring basis. For example, in resequencing applications in which a homopolymeric stretch of nucleotide is to be resequenced to determine the number of residues, repeated cycles can be performed with only one 2'-modified reversible terminator, which is complementary to the repeated base in the homopolymeric tract.

The sequencing reaction can be carried our in any number of formats. For example, the reaction may be performed in solution. In other embodiments, the reaction is performed on a solid phase, such as a microarray or on a microbead, in which the DNA template is associated with a solid support. Useful types of solid supports include plates, beads, microbeads, whiskers, fibers, combs, hybridization chips, membranes, single crystals, ceramics, and self-assembling monolayers. Nucleic acids may be attached to the solid support by covalent binding such as by conjugation with a coupling agent or by non-covalent binding such as electrostatic interactions, hydrogen bonds or antibody-antigen coupling, or by combinations thereof. There are a wide variety of known methods of attaching nucleic acids to solid supports. See for example PCT Application Nos. US98/21193, PCT US99/14387 and PCT US98/05025; and WO98/50782.

A nucleic acid template may be directly attached to the surface by either the 5' or the 3' end. A template may also be attached via an oligonucleotide, e.g., an oligonucleotide primer. For example, in some applications, it may be desirable to perform the sequencing reaction on a microarray format in which an oligonucleotide primer attached to the surface is annealed to the template and crosslinked. Alternatively, hybridization of the template to an oligonucleotide may also be performed in solution, followed by attachment to a solid support, e.g., via a linker present on the oligonucleotide primer. Because the array consists of discrete, resolvable positions, each target polynucleotide present will generate a series of distinct signals indicative of the incorporation of modified 2' reversible terminator nucleotides. Many different microarray formats can be used, including single molecule microarray formats such as those described, e.g., in U.S. Pat. No. 6,787,308 and U.S. Patent Application Publication No. 20020164629. These references provide additional exemplary guidance in attaching nucleic acids to solid surfaces.

Sequence determination can be performed adding different 2'-modified reversible terminator nucleotides, e.g., terminator nucleotides corresponding to each of the four naturally occurring nucleotides, simultaneously or sequentially. For example, when the nucleotides are added simultaneously, an added terminator nucleotide that pairs with the nucleotide present in the template DNA is incorporated into the chain and stops chain growth. The 2'-blocking group is removed to provide for further chain elongation. Detection can occur either when the nucleotide is incorporated into the chain or at a subsequent step, e.g., when the blocking group is removed, or when a label present on a base via a linker is removed. In some embodiments, the 2'-blocking group can be removed in a buffer or wash that also removes all unincorporated nucleotides.

In other embodiments, the nucleotides are added sequentially.

Systems

The invention also provides a system for determining the sequence of a nucleic acid. Such a system includes at least one container comprising a 2' reversible terminator nucleotide. Typically, the system comprises a plurality of containers, e.g., for performing sequence determination reactions in parallel. The system also includes at least one thermal modulator (e.g., a thermocycling device, etc.) operably connected to the container to modulate temperature in the container, and/or (c) at least one fluid transfer component (e.g., an automated pipettor, etc.) that transfers fluid to and/or from the container. Thermocycling devices, some of which are embodied in microfluidic devices, and various fluid transfer devices suitable or adaptable for use in the systems of the invention are generally known in the art. The system optionally further includes at least one detector operably connected to the container to detect detectable signals produced in the container. The system typically further includes at least one controller operably connected to the thermal modulator to effect modulation of the temperature in the container and/or to the fluid transfer component to effect transfer of the fluid to and/or from the container.

The systems of the invention include various signal detectors. The detection components detect a signal that is indicative of the incorporation of a 2'-reversible terminator nucleotide. For example, the detector optionally monitors a plurality of optical signals, which correspond in position to "real time" results. Signals generated during the sequencing reactions can be detected using any method that can read the activity of a reporter molecule. Suitable signal detectors for use, in these systems detect, e.g., fluorescence, phosphorescence, radioactivity, mass, concentration, pH, charge, absorbance, refractive index, luminescence, temperature, magnetism, or the like. For example, fluorescence is optionally detected by detectors or sensors, such as photomultiplier tubes (PMTs), charge-coupled devices (CCDs), intensified CCDs, photodiodes, avalanche photodiodes, optical sensors, scanning detectors, or the like. Exemplary detection systems are described, e.g., in Skoog et al., Principles of Instrumental Analysis, 5.sup.th Ed., Harcourt Brace College Publishers (1998) and Currell, Analytical Instrumentation: Performance Characteristics and Quality, John Wiley & Sons, Inc. (2000)). Detectors such as these are readily available from various commercial sources including, e.g., Applied Biosystems (Foster City, Calif.).

The systems of the invention also typically include controllers that are operably connected to one or more components (e.g., analytic components, synthetic components, thermal modulator, fluid transfer components, detectors, etc.) of the system to control operation of the components. Controllers are generally included either as separate or integral system components e.g., to receive data from detectors, to effect and/or regulate temperature in the containers, to effect and/or regulate fluid flow to or from selected containers, or the like. Controllers and/or other system components is/are optionally coupled to an appropriately programmed processor, computer, digital device, or other information appliance (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor which is often a cathode ray tube ("CRT") display, a flat panel display (e.g., active matrix liquid crystal display, liquid crystal display, etc.), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a GUI, or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming, e.g., such as controlling fluid flow regulators in response to fluid weight data received from weight scales or the like.

Kits

The invention also provides kits for sequence determination. Such kits can include at least one 2'-modified reversible terminator nucleotide. The 2'-terminator nucleotide optionally includes at least one label (e.g., a radioisotope, a fluorescent dye, a mass-modifying group, or the like). In some embodiments, the kit additionally comprises a reagent for removing the blocking modification present on the terminator nucleotide. Kits of the invention can also include additional components such as one or more of the following: an extendable nucleotide, a polymerase for performing the reaction, buffers, or enzyme components or reagents that are needed to detect a signal.

In some embodiments, a kit comprises one or more labeled 2'-modified reversible terminator nucleotides as set forth below:

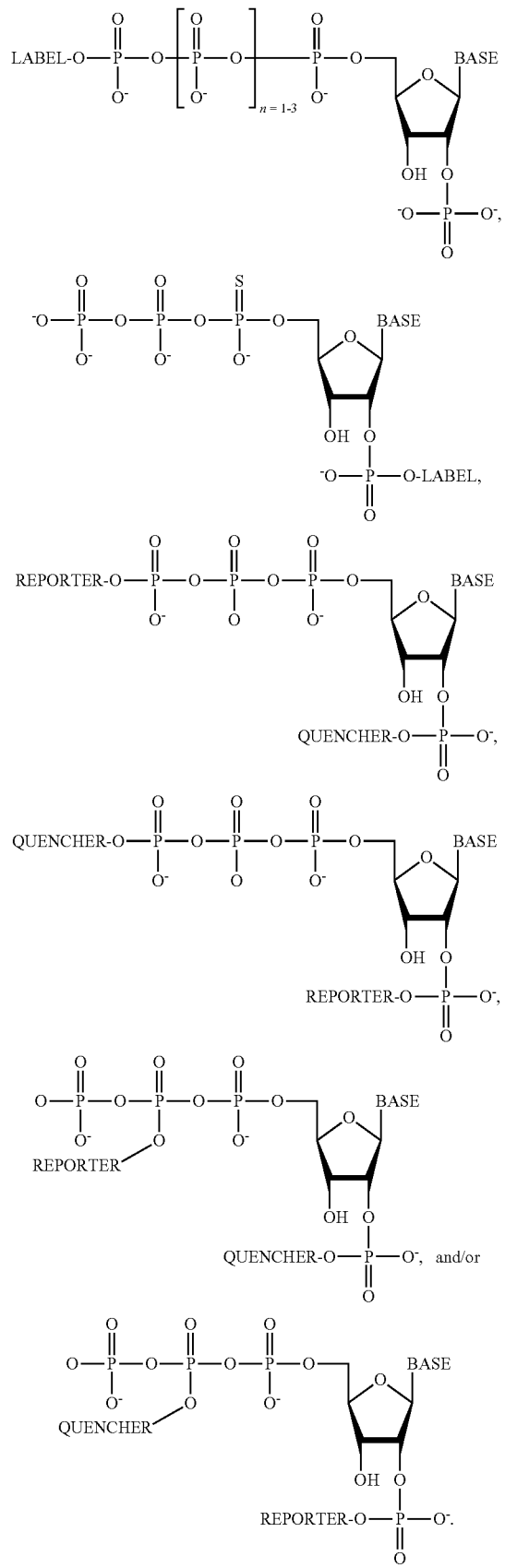

EXAMPLES

It is understood that the examples and embodiments described herein are for illustrative purposes only and are not intended to limit the scope of the claimed invention. It is also understood that various modifications or changes in light the examples and embodiments described herein will be suggested to persons skilled in the art and are to be included within the spirit and purview of this application and scope of the appended claims.

Example 1

Synthesis of a Labeled Tetraphosphate Nucleotide

A prophetic example of a method for synthesizing a 2'-phosphate labeled (TAMRA)-Uridine, tetraphosphate is shown below. As shown, this method takes advantage of solid phase synthesis techniques and readily available starting materials, but the scheme is also readily amenable to solution-phase synthesis with slight modifications. Similarly, the scheme can be readily adapted for the synthesis of other dye labeled nucleotides with slight modifications. For example, the TAMRA-cpg in the first step in the scheme can alternatively be replaced by a suitably protected and modified dye moiety containing a reactive hydroxyl function. Uridine 3'-tBDSilyl CED Phosphoramidite (ANP-5684, Chemgenes, Wilmington, Mass.) is coupled to 3'-Tamra CPG (Glen Research, Sterling, Va.). Following removal of the 5'-DMT protecting group, the 5'-OH group is reacted with salicyl phosphorochloridite and pyrophosphate, followed by oxidation (Ludwig and Eckstein, J. Org. Chem. 1989, 54, 631-635) and cleavage from support to yield the desired compound.

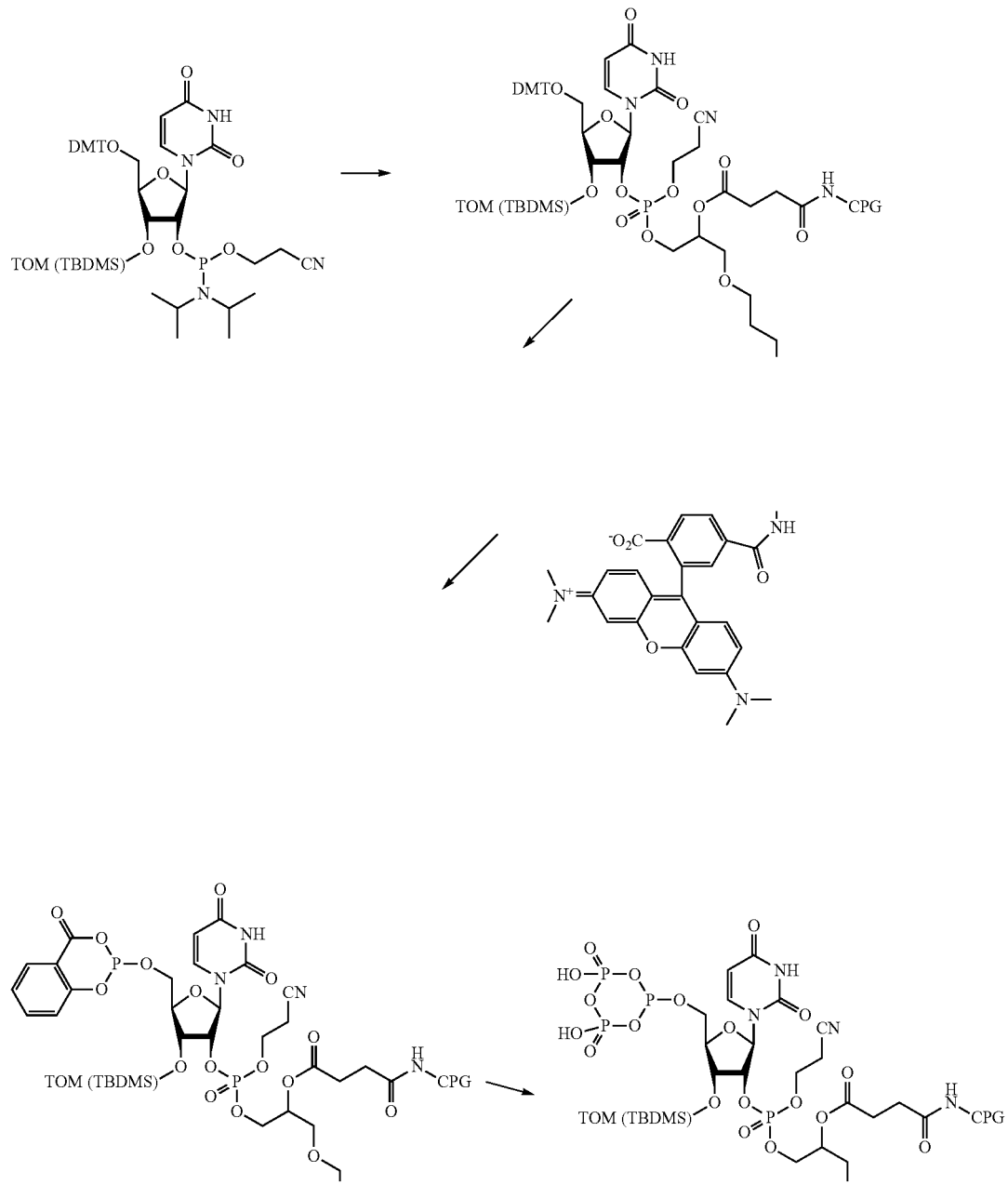

23    24

-continued

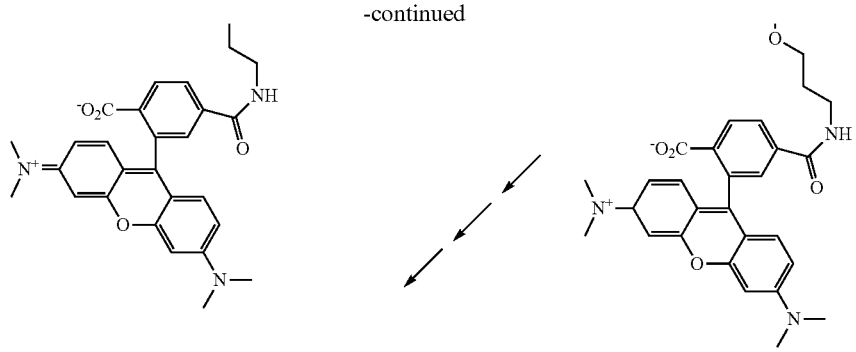

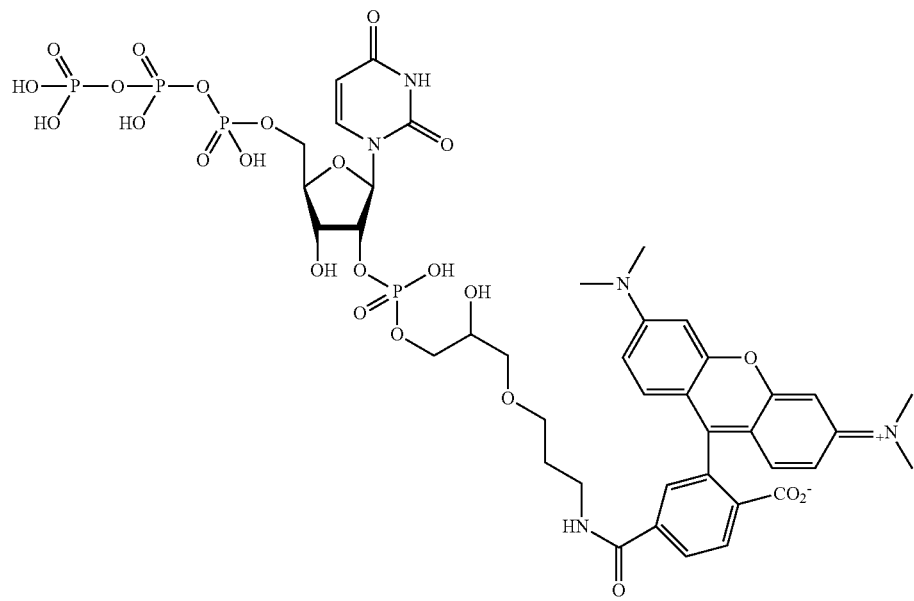

Example 2

Synthesis of a Labeled Tetraphosphate Nucleotide

A prophetic example for a more general method for synthesizing a 2'-phosphate labeled, and 2'-phosphate labeled-terminal phosphate labeled nucleoside polyphosphates is shown below. As shown, this method takes advantage of solid phase synthesis techniques and readily available starting materials, but the scheme is also readily amenable to solution-phase synthesis with slight modifications. For example, the 3'-Amino-Modifier C7 CPG in the first step in the scheme can alternatively be replaced by a suitably protected amino-alkyl-linker with a reactive hydroxyl function. A nucleoside 3'-tBDSilyl CED Phosphoramidite (e.g., ANP-5684, Chemgenes, Wilmington, Mass.) is coupled to 3'-Amino-Modifier C7 CPG (Glen Research, Sterling, Va.). Following the coupling step, the 2'-phosphorus can be modified to P=O, P=S, P=Se, or P:BH3, as needed by choosing the appropriate reagents known in the art. In the next three steps, the 5'-DMT protecting group is removed, the resulting 5'-OH group is reacted with salicyl phosphorochloridite, and the salicyl group is displaced by pyrophosphate (Ludwig and Eckstein, J. Org. Chem. 1989, 54, 631-635). Alternatively, a polyphosphate, e.g., tripolyphosphate, may be employed for other modifications. Once again, the alpha-phosphorus may now be modified to P=O, P=S, P=Se, or P:BH3, as needed by choosing the appropriate reagents known in the art. In the next step, the cyclic polyphosphate may be hydrolyzed or reacted with a dye or other label with a nucleophilic group for terminal phosphate labeling. Finally, the molecule is cleaved from the support, deprotected, and reacted with a reactive dye derivative such as an NHS ester.

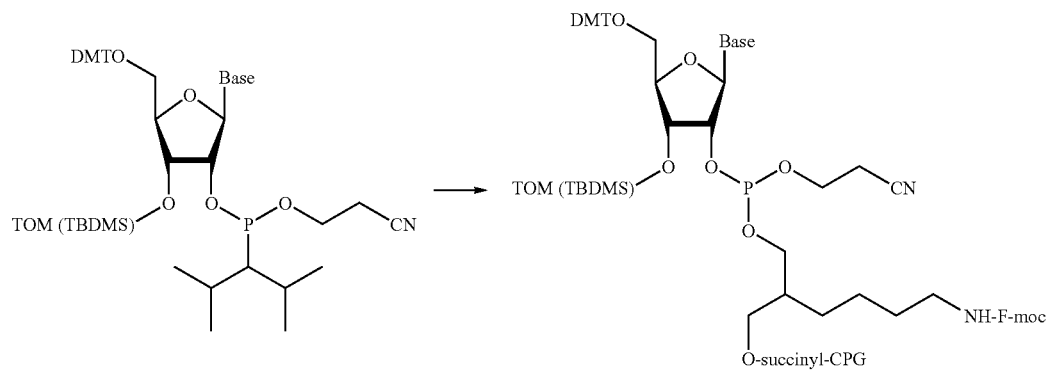
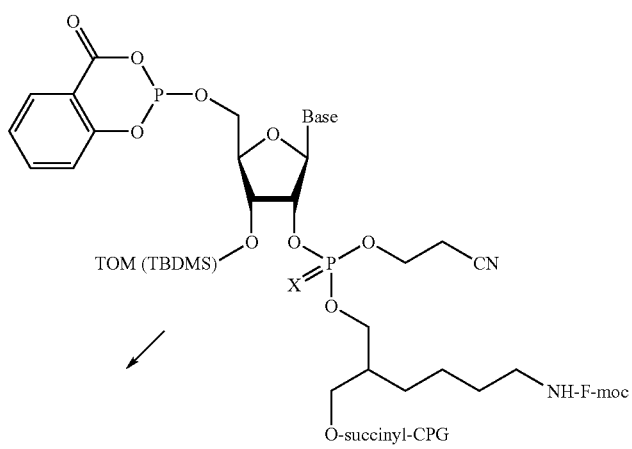
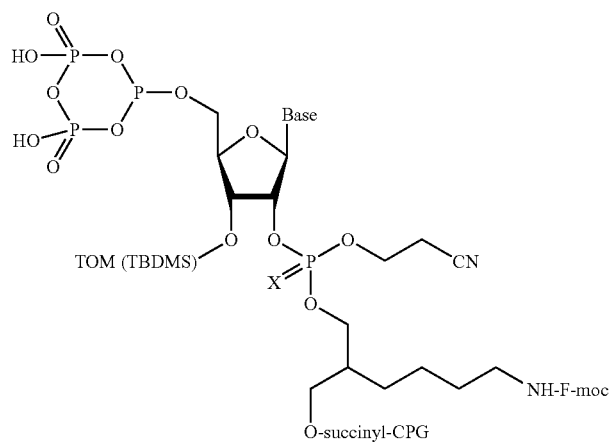
Several steps

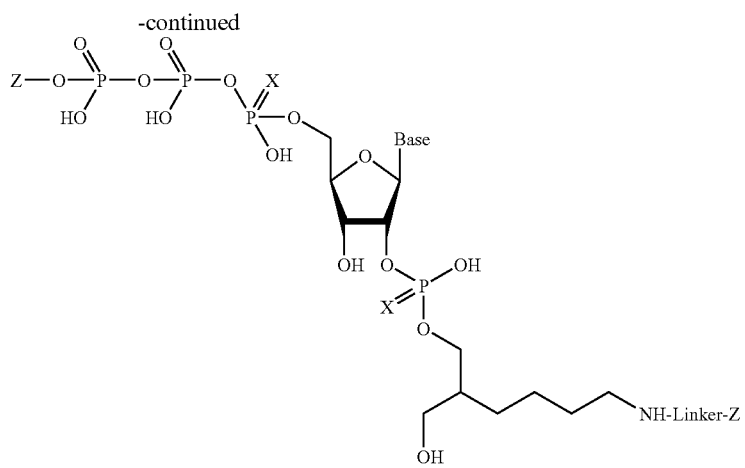

X = O, S, Se, BH3, or NH
Z = H, Label, Reporter, Quencher

Example 3

Synthesis of a Labeled Tetraphosphate Nucleotide

Another prophetic example for a general method for synthesizing a cleavable 2'-phosphate labeled, and 2'-phosphate labeled, terminal phosphate labeled nucleoside polyphosphates is shown below. As shown, this method takes advantage of solid phase synthesis techniques and readily available starting materials, but the scheme is readily amenable to solution-phase synthesis with slight modifications. For example, the 3'-Thiol-Modifier C3 S—S CPG in the first step in the scheme can alternatively be replaced by a suitably protected alkyl-thiol-linker with a reactive hydroxyl function. A nucleoside 3'-tBDSilyl CED Phosphoramidite (e.g., ANP-5684, Chemgenes, Wilmington, Mass.) is coupled to 3'-Thiol-Modifier C3 S—S CPG (Glen Research, Sterling, Va.). Following the coupling step, the 2'-phosphorus can be modified to P=O, P=S, P=Se, or P:BH3, as needed by choosing the appropriate reagents known in the art. In the next three steps, the 5'-DMT protecting group is removed, the resulting 5'-OH group is reacted with salicyl phosphorochloridite, and the salicyl group is displaced by pyrophosphate (Ludwig and Eckstein, J. Org. Chem. 1989, 54, 631-635). Alternatively, a polyphosphate, e.g., tripolyphosphate may be employed for other modifications. Once again, the alpha-phosphorus may now be modified to P=O, P=S, P=Se, or P:BH3, as needed by choosing the appropriate reagents known in the art. In the next step, the cyclic polyphosphate may be hydrolyzed or reacted with a dye or other label with a nucleophilic group for terminal phosphate labeling. Finally, the molecule is cleaved from the support, deprotected, and a reactive thiol function is generated by reduction of the disulfide linkage. This can be reacted with a thiol reactive dye derivative such as a maleimide derivative.

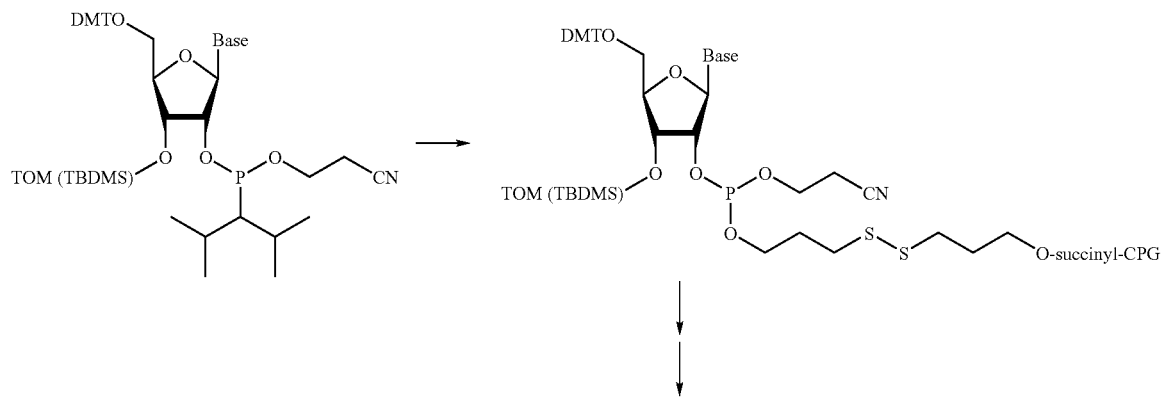

-continued

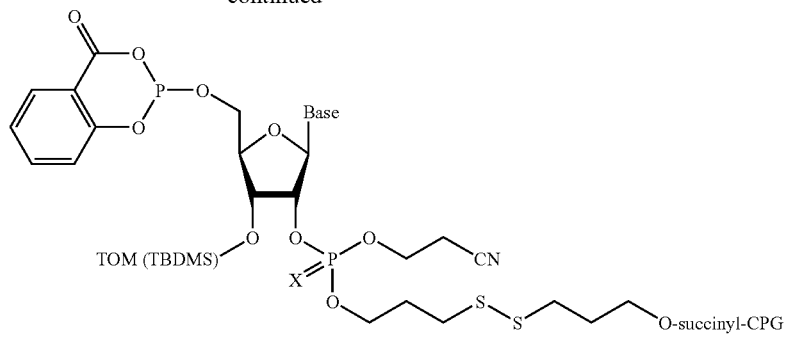

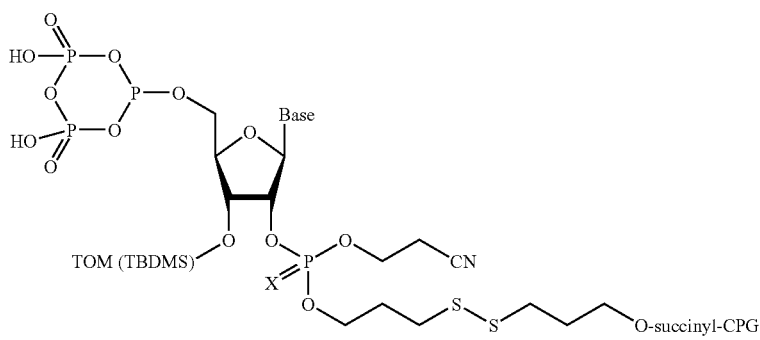

Several steps

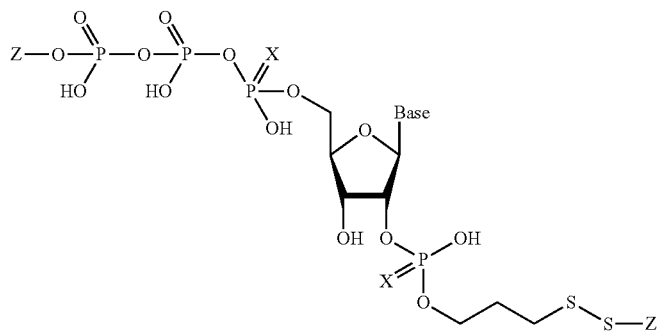

X = O, S, or NH
Z = H, Label, Reporter, Quencher

Example 4

Four Color Simultaneous Sequencing

A prophetic example for a general method for 4-color simultaneous sequencing with all four bases is described. In certain embodiments, the present invention provides methods for determining a nucleic acid sequence by performing successive cycles of primer extension along a single stranded template using all four nucleotides simultaneously. In certain embodiments the sequencing reactions are performed on templates attached to beads, which are immobilized in a flow cell or on a solid support. The cycles comprise sequential steps of extension, detection, label removal, and deblocking. In certain embodiments the methods, make use of 2'-terminator nucleotides labeled at the base through a cleavable linker, where a unique and distinguishable label (e.g., a fluorophore) is used for each of the four bases. In the exemplary scheme shown below, the extension is accompanied by a fluorescent signal generated by virtue of incorporation, that is specific to the base incorporated. The label is removed via photochemical or chemical cleavage, and the blocking groups are subsequently removed by treatment with a phosphatase.

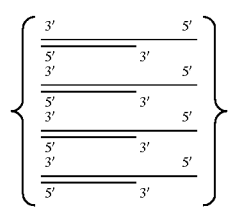
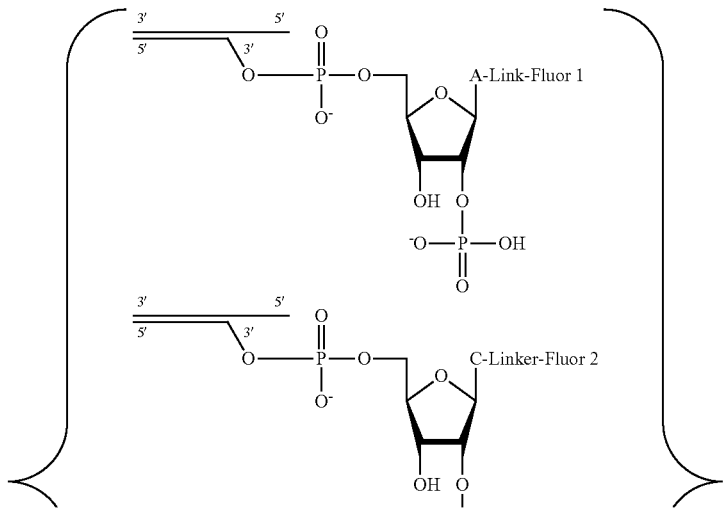
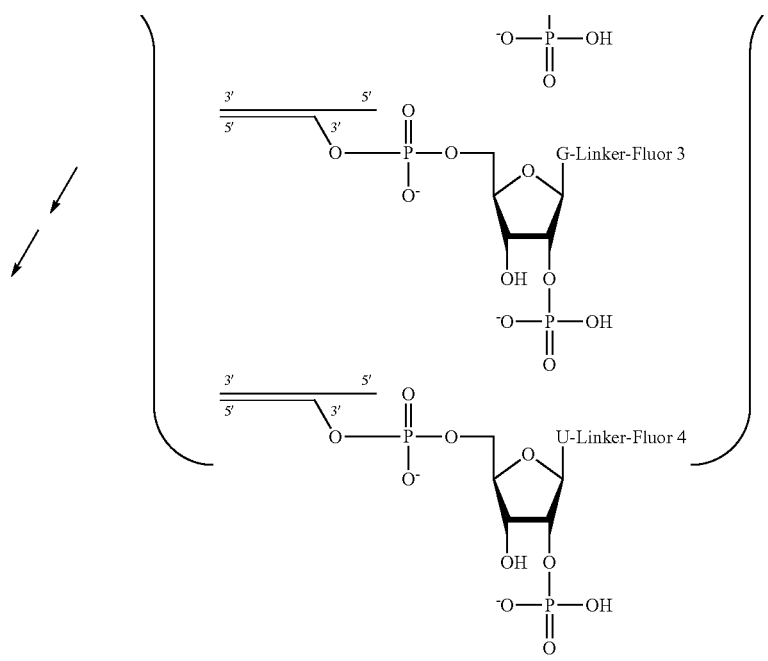

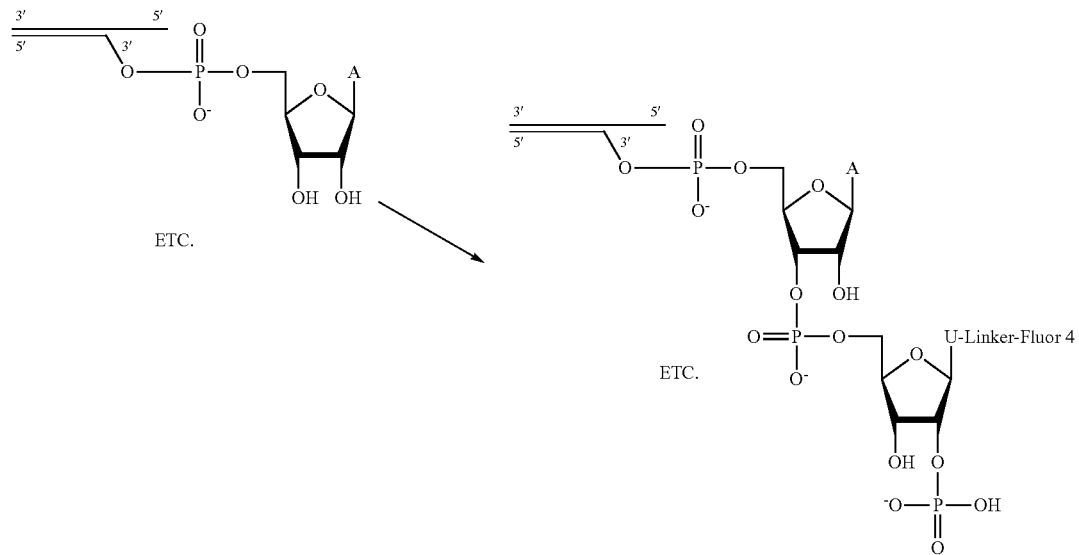

Example 5

Pour Color Simultaneous Sequencing

A prophetic example for a general method for 4-color simultaneous sequencing with all four bases is described. In certain embodiments, the present invention provides methods for determining a nucleic acid sequence by performing successive cycles of primer extension along a single stranded template using all four nucleotides simultaneously. In certain embodiments the sequencing reactions are performed on templates attached to beads, which are immobilized in a flow cell or on a solid support. The cycles comprise sequential steps of extension, detection, label removal, and deblocking. In certain embodiments the methods make use of 2'-terminator nucleotides labeled at the 2'-phosphate, where a unique and distinguishable label (e.g., a fluorophore) is used for each of the four bases. In the exemplary scheme shown below, the extension is accompanied by a fluorescent signal generated by virtue of incorporation, that is specific to the base incorporated. The label and blocking groups are subsequently removed by treatment with a phosphodiesterase and a phosphatase. If needed, the phosphate backbone is modified with phosphorothioate linkages.

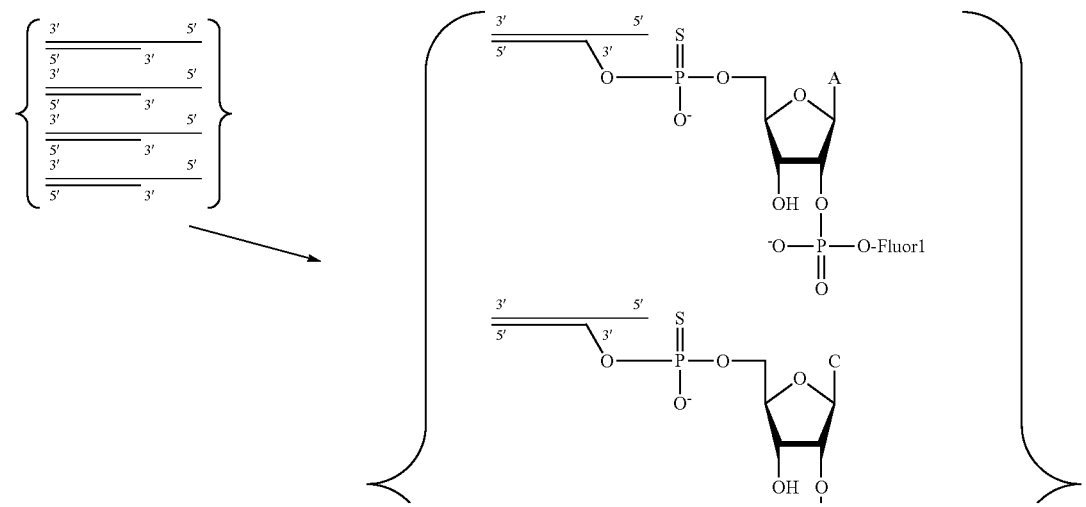

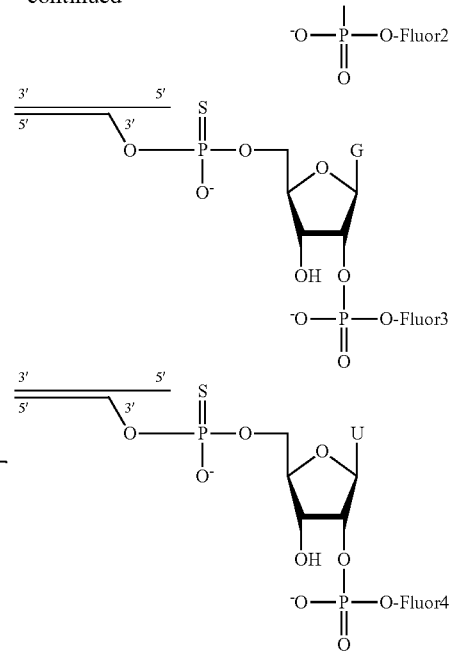

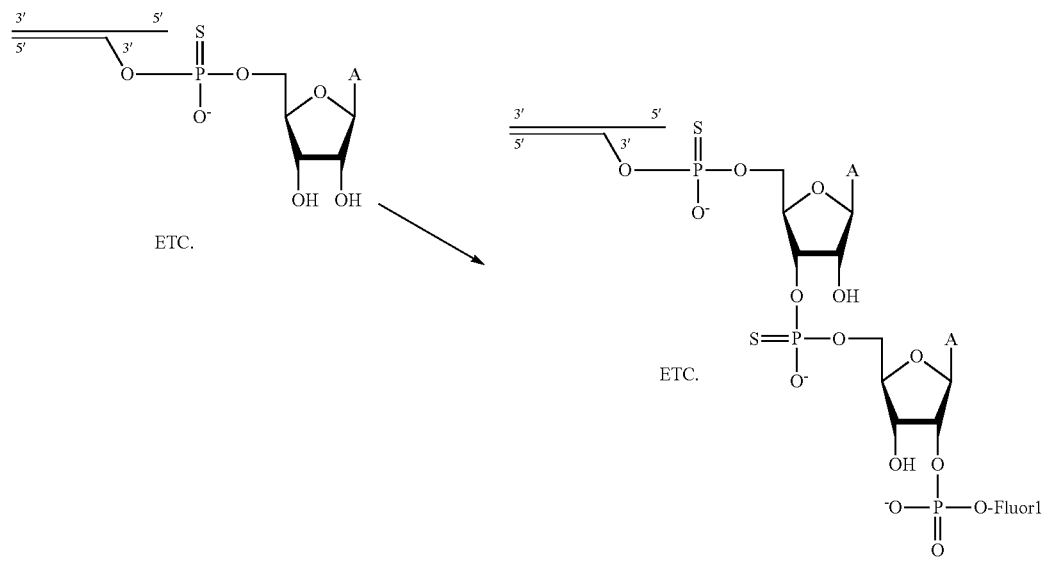

ETC.

Example 6

Four Color Simultaneous Sequencing

A prophetic example for a general method for 4-color simultaneous sequencing with all four bases is described. In certain embodiments, the present invention provides methods for determining a nucleic acid sequence by performing successive cycles of primer extension along a single stranded template using all four nucleotides simultaneously. In certain embodiments the sequencing reactions are performed on templates attached to beads, which are immobilized in a flow cell or on a solid support. The cycles comprise sequential steps of extension, detection, label removal, and deblocking. In certain embodiments the methods make use of 2'-terminator nucleotides labeled at the 2'-phosphate that is attached to the 2'-position through a sulfur, where a unique and distinguishable label (e.g., a fluorophore) is used for each of the four bases. In the exemplary scheme shown below, the extension is accompanied by a fluorescent signal generated by virtue of incorporation, that is specific to the base incorporated. The label and blocking groups are subsequently removed by treatment with a metal ion such as Ag+, Hg++, iodine, etc.

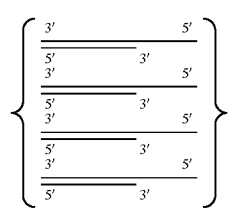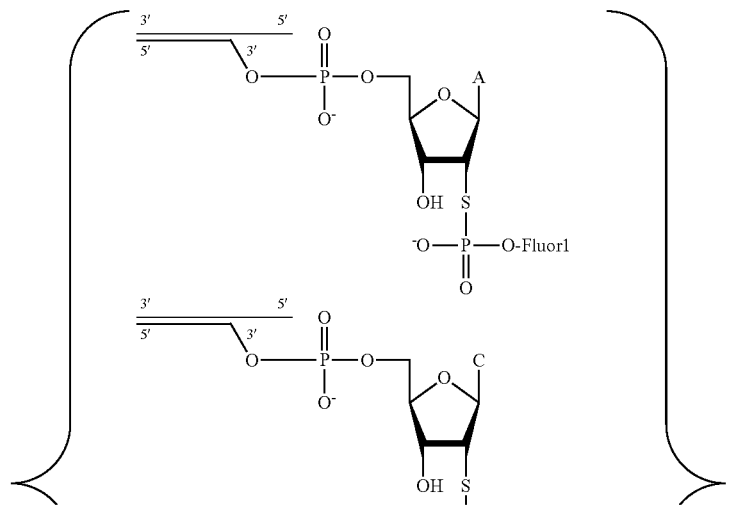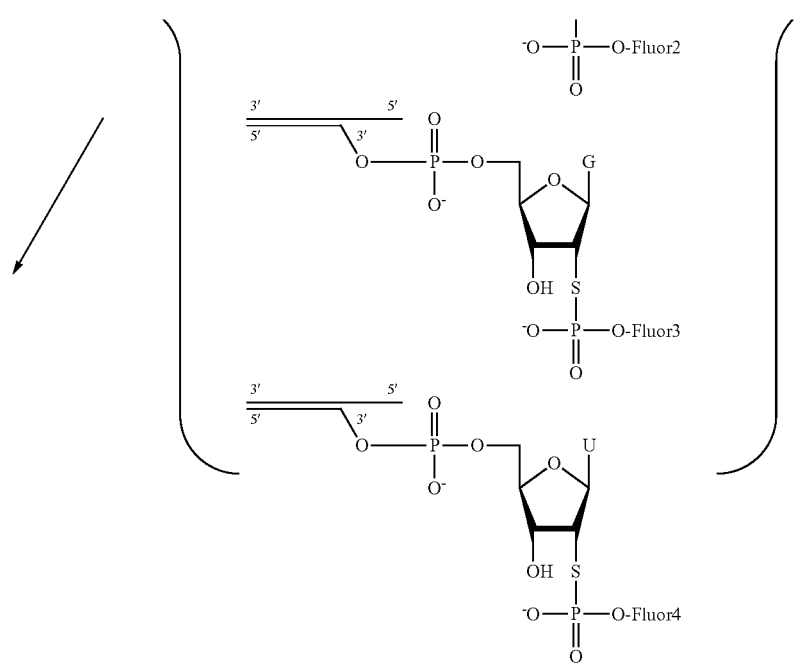

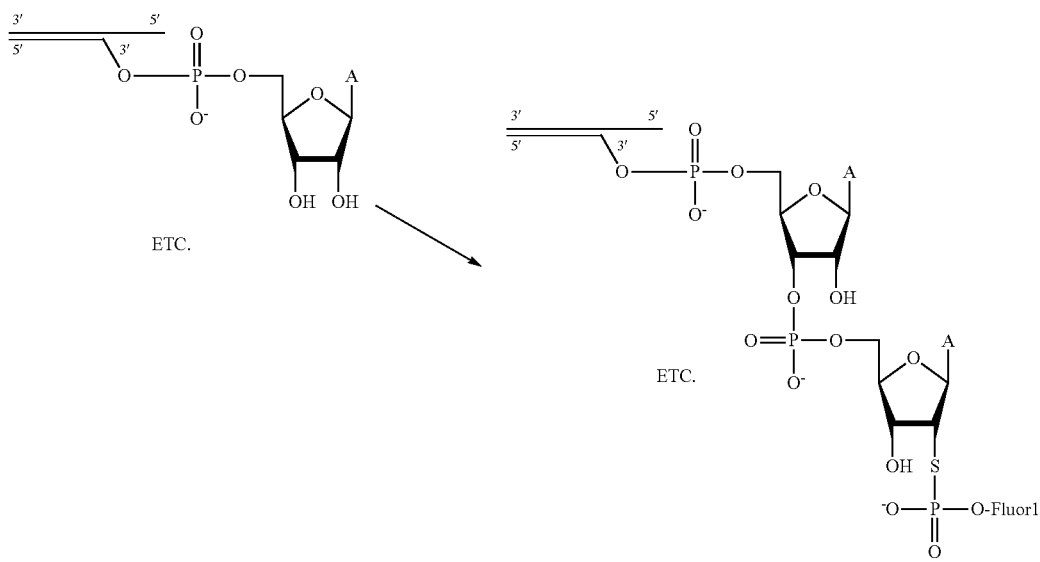

ETC.

Example 7

Sequencing by Cycled Primer Extension with Tetraphosphate Nucleotides

This example illustrates the application of tetraphosphate nucleotides (i.e., 2'-modified reversible terminator nucleotides) in thermal cycled template directed primer extension and sequencing reactions. These reactions were performed with a G46E Q601R D640G S671F E678G (or "GQDSE") CS6 DNA polymerase, though they could be performed with other DNA polymerases modified to readily incorporate 2'-modified reversible terminator nucleotides. CS6 chimeric polymerases are further described in, e.g., U.S. Pat. Application Publication No. 2004/0005599. Primer extension reactions were performed in a buffer consisting of 80 mM Tricine (pH 7.75), 100 mM KOAc, and 1.0 mM Mn(OAc)$_2$. Each reaction (50 µl) contained 0.04 µM GQDSE CS6 DNA polymerase, 2 units/µl rTth Thermostable Pyrophosphatase (Roche Molecular Systems, Inc., Branchburg N.J.), 0.02 µM 5'-FAM labeled oligoribonucleotide primer, 0.04 µM oligodeoxynucleotide template, and 0.2 µM DNA polymerase optimized aptamer. More specifically, the primer and template sequences were as follows:

```
Primer:
5'-FAM-AGCAACAAGUUUAGUUCGUUCGAGCCGUGCGA-3'

Template:
3'-ACGTTGTTCAAATCAAGCAAGCTCGGCACGCTACGTACGTACGT-5',
where E = 3' phosphate.
``` where E=3' phosphate.

Reactions were thermal cycled in an Applied Biosystems GeneAmp® PCR System 9700. A 2 µl aliquot was removed at 50° C. and added to 38 µl 1 mM EDTA. The extension reaction was initiated at 50° C. with the addition of 2 µl mixture of 250 µM each tetraphosphate nucleotide (2'-PO$_4$-NTP) and then incubated at 64° C. for 5 minutes. The temperature was reduced to 15° C. and a 2 µl aliquot of the extension reaction was removed for analysis and added to 38 µl 1 mM EDTA to stop the reaction. The 2'-monophosphate blocking group was removed by addition of 2 µl 1 unit/µl CIAP (alkaline phosphatase, calf intestinal, Promega catalog (2005) # M182A) and incubation at 27° C. for 5 minutes. The CIAP was inactivated by incubation at 85° C. for 5 minutes. Three additional rounds of extension and de-blocking were performed as described above. The 2 µl of stopped extension reaction was diluted into 18 µl GeneScan™-120LIZ™ Size Standard (Applied Biosystems, Foster City, Calif., P/N 4322362): HiDi™ formamide (Applied Biosystems, Foster City, Calif., P/N 311320) (1:40) and incubated at 95° C. for 5 minutes.

Figure 2:
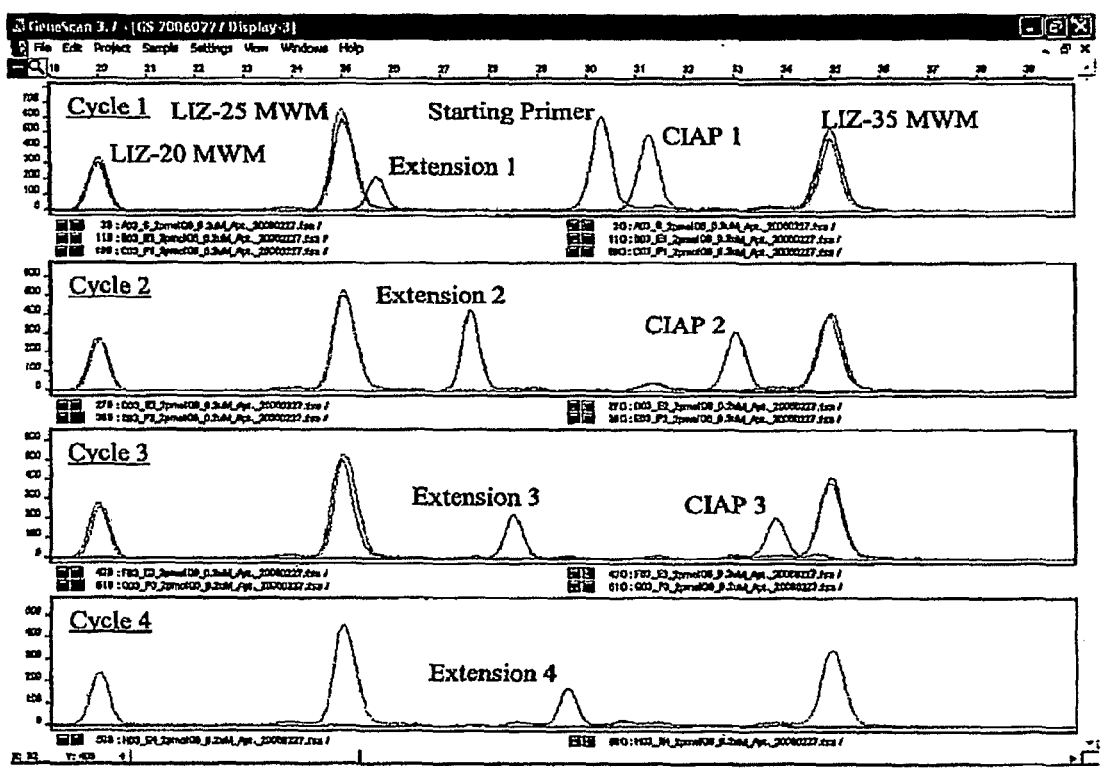
FIG. 2 shows FAM dye-labeled primer extension products from four rounds of extension and de-blocking according to one embodiment of the invention.

The extension reactions were analyzed by capillary electrophoresis using an Applied Biosystems 3100 Genetic Analyzer with Foundation Data Collection version 2.0 software and final analysis with Applied Biosystems GeneScan™ version 3.7 software. FIG. 2 shows the FAM dye-labeled primer extension products from four rounds of extension and de-blocking. For cycle 1 the starting primer, before addition of nucleotides, is shown as are the extension products before and after dephosphorylation with CLAP. For cycles 2 and 3 the extension products before and after dephosphorylation are shown while for cycle 4 the post CIAP product was not analyzed so only the extension product before dephosphorylation is shown. The incorporation of a 2'-PO$_4$-NTP causes the extension product to migrate faster than the starting primer, relative to the 120LIZ size standards, due to the extra negative charge of the 2'-PO$_4$. After incubation with CIAP the 2'-PO$_4$ is removed and the extension product migrates slower than the starting primer relative to the size standards, as expected. This is clearly seen in FIG. 2 where the starting primer migrates at approximately 30 bases relative to the size standard, the extension product migrates at approximately 26 bases, and the extension product after CIAP incubation migrates at approximately 31 bases. The extension products for each cycle, before and after CIAP incubation, migrate as progressively larger products relative to the 120LIZ size standards as would be expected for primer extension products of increasing size.

Example 8

Sequencing by Cycled Primer Extension with Dye Labeled 2'-Terminator Nucleotides This example illustrates the application of dye labeled 2'-PO$_4$-NTPs in thermal cycled template directed primer extension and sequencing reactions. Dye labeled 2'-PO$_4$-NTPs were used in the last extension step only to demonstrate sequence specific incorporation of the correct 2'-PO$_4$-NTP. For example, in a three cycle extension reaction unlabeled 2'-PO$_4$-NTPs are used in the first two extension cycles and dye-labeled 2'-PO$_4$-NTPs were used in the third extension step. These reactions were performed with GQDSE CS6 DNA polymerase, though they could be performed with other DNA polymerases modified to readily incorporate 2'-modified NTPs. Primer extension reactions were performed in a buffer consisting of 80 mM Tricine (pH 7.75), 100 mM KOAc, and 1.0 mM Mn(OAc)$_2$. Each reaction (50 µl) contained 0.1 µM GQDSE CS6 DNA polymerase, 2 units/µl rTth Thermostable Pyrophosphatase (Roche Molecular Systems, Inc., Branchburg N.J.), 0.02 µM 5'-FAM labeled oligoribonucleotide primer, 0.04 µM oligodeoxynucleotide template, and 0.5 µM DNA polymerase optimized aptamer. More specifically, the primer and template sequences were as follows:

```
Primer:
5'-FAM-AGCAACAAGUUUAGUUCGUUCGAGCCGUGCGA-3'

Template:
3'-ECGTTGTTCAAATCAAGCAAGCTCGGCACGCTACGTACGTACGT-
5',
where E = inverted dA.
``` where E=inverted dA.

Reactions were thermal cycled in an Applied Biosystems GeneAmp® PCR System 9700. A 2 µl aliquot was removed at 27° C. and added to 18 µl 1 mM EDTA. The extension reaction was initiated at 27° C. with the addition of 2 µl 250 µM each 2'-PO$_4$-NTPs or if the last extension step 2 µl 25 µM each dye-labeled 2'-PO$_4$-NTPs and then incubated at 64° C. for 5 minutes. The temperature was reduced to 15° C. and a 2 µl aliquot of the extension reaction was removed and added to 18 µl 1 mM EDTA. The 2'-PO$_4$ blocking group was removed by addition of 2 µl 1 unit/µl CIAP (alkaline phosphatase, calf intestinal, Promega catalog #M182A (this is the old catalog #, the new number is M1821) and incubation at 27° C. for 5 minutes. The CIAP was inactivated by incubation at 85° C. for 5 minutes. Additional rounds of extension and de-blocking were performed as above. The EDTA stopped reaction was filtered through Sephadex® G-50 (Sigma-Aldrich part number G5080) to remove un-incorporated dye-labeled 2'-PO$_4$-NTPs. 2 µl of the filtered extension reaction was diluted into 18 µl GeneScan™-120LIZ™ Size Standard (Applied Biosystems P/N 4322362): HiDi™ formamide (Applied Biosystems P/N 311320) (1:40) and incubated at 95° C. for 3 minutes.

Figure 3:
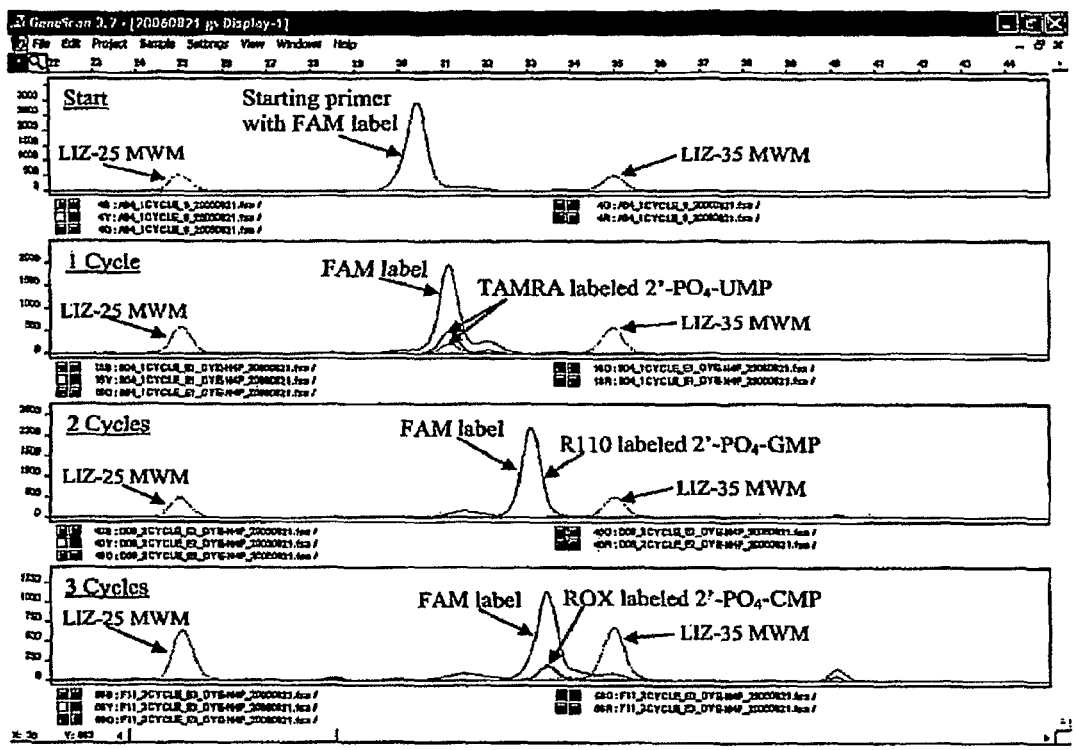
FIG. 3 shows cycled primer extension using dye-labeled 2'-modified reversible terminators according to one embodiment of the invention.

The extension reactions were analyzed by capillary electrophoresis using an Applied Biosystems 3100 Genetic Analyzer with Foundation Data Collection version 2.0 software and final analysis with Applied Biosystems GeneScan™ version 3.7 software. FIG. 3 shows the dye-labeled starting primer and the dye-labeled extension product of 1, 2, and 3 rounds of SBS. The instrument collects the dye emission data in five channels or bins which are represented as peaks in traces in FIG. 3. The spectral emission of a single dye can fall into one or more bins and thus be represented as one or more peaks in the figure. In the example R110 and FAM fall in the same bin and thus only one peak is seen. All the extension products have a 5'-FAM label plus a 3' dye-labeled 2'-PO$_4$-NTP. For the single base extension the templating base is an A and TAMRA-labeled 2'-PO$_4$-UMP is incorporated. Relative to the GeneScan™-120LIZ™ Size Standard (Applied Biosystems, Foster City Calif.) the single base extension product migrates at approximately 31 bases compared to the starting FAM-labeled primer which migrates between 30 and 31 bases relative to the size standard. For the 2 cycle extension reaction the second templating base is C and R110-labeled 2'-PO$_4$-GMP is incorporated. The two base primer extension product migrates at approximately 33 bases relative to the size standard. For the 3 cycle extension reaction the third templating base is G and ROX-labeled 2'-PO$_4$-CMP is incorporated. The three base extension product migrates between 33 and 34 bases relative to the size marker. Sequence specific incorporation of dye-labeled 2'-PO$_4$-NTPs is demonstrated by the progressively longer products, relative to the size standard, for each extension cycle in combination with the identifiable spectra of each incorporated dye-labeled 2'-PO$_4$-NTP.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of sequencing at least a portion of a template nucleic acid, the method comprising:
    (a) incubating in a reaction mixture at least one template nucleic acid with at least one DNA polymerase, a plurality of different 2'-modified reversible terminator nucleotides, each different 2'-modified reversible terminator nucleotide comprising a different base and further comprising a blocking group at a 2' position of the sugar moiety, wherein the blocking group is a phosphate, and at least one primer nucleic acid that is complementary to at least a subsequence of the template nucleic acid, whereby the polymerase extends the primer nucleic acid to produce at least one primer extension product that incorporates in a sequence specific manner the correct 2'-modified reversible terminator nucleotide at a 3'-terminal end of the primer extension product;
    (b) removing the blocking group from the 2' position of the 2'-modified reversible terminator nucleotide at the 3'-terminal end of the primer extension product with an enzyme that removes the phosphate;
    (c) identifying the correct 2'-modified reversible terminator nucleotide in the primer extension product prior to and/or during (b); and
    (d) repeating (a)-(c) one or more times,
whereby at least a portion of a base sequence of the template nucleic acid is determinable from the identified 2'-modified reversible terminator nucleotide, thereby sequencing at least the portion of the template nucleic acid.

2. The method of claim 1, wherein the enzyme that removes the 2' position phosphate is a phosphatase.

3. The method of claim 1, wherein the enzyme that removes the 2' position phosphate is an exonuclease III.

4. The method of claim 1, wherein the enzyme that removes the 2' position phosphate is an endonuclease IV.

5. The method of claim 1, wherein the enzyme that removes the 2' position phosphate is polynucleotide kinase.

6. The method of claim 1, wherein the enzyme that removes the 2' position phosphate is a phosphodiesterase or a combination of a phosphodiesterase and a phosphatase.

7. The method of claim 1, wherein the 2' modified reversible terminator nucleotide is

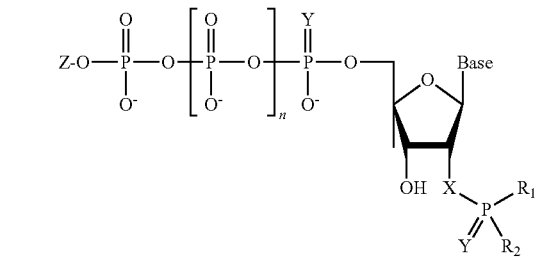

$n$ = 1-3
X = O, NH, S
Y = O, S, Se, BH3
Z = H, DYE
R1, R2 = INDEPENDENTLY, OH, ALKYL, ARYL, ALKOXY, ALKYLAMINO, THIOALKYL, (OPO2)$n$OH, DYE, QUENCHER, LINKER + LABEL ETC.

8. The method of claim 1, wherein the 2'-modified reversible terminator nucleotide is labeled with at least one labeling moiety.

9. The method of claim 8, wherein the labeling moiety comprises a fluorescent dye, a luminescent molecule, or a radioisotope.

10. The method of claim 9, wherein the labeling moiety is a fluorescent dye.

11. The method of claim 8, where in the labeling moiety is attached to the 2'-modified reversible terminator nucleotide at the base via a cleavable linker, and the method further comprises a step of cleaving the linker.

12. The method of claim 8, wherein the 2'-modified reversible terminator nucleotide is linked to two labeling moieties that comprise a donor and an acceptor.

13. The method of claim 12, wherein the donor and the acceptor are a reporter and a quencher pair.

14. The method of claim 12, wherein the two labeling moieties are capable of undergoing fluorescence resonance energy transfer.

15. The method of claim 1, wherein the reaction mixture comprises four different 2'-modified reversible terminator nucleotides, each having a different base and labeled with a different labeling moiety.

16. The method of claim 1, wherein the detecting step comprises detecting pyrophosphate generated upon incorporation of the 2'-modified reversible terminator nucleotide.

17. The method of claim 1, wherein the 2'-modified reversible terminator nucleotide comprises a 2'-monophosphate-3'-hydroxyl nucleotide.

18. A method of sequencing at least a portion of a template nucleic acid, comprising:
   a) incubating the template nucleic acid in a reaction mixture comprising a primer, a polymerase, and a plurality of different 2'-modified reversible terminator nucleotides, each different 2'-modified reversible terminator nucleotide comprising a different base, and further comprising a phosphate as a blocking group at the 2' position of the sugar moiety, under conditions in which the primer anneals to the template nucleic acid and is extended by the polymerase present in the reaction to form an extended product;
   b) determining the presence of a signal indicative of sequence specific incorporation of the correct 2'-modified reversible terminator nucleotide into the extended product;
   c) incubating the extended product with an enzyme that removes the phosphate at the 2' position present on the reversible terminator nucleotide;
   d) repeating steps a) to c) a desired number of times to determine the sequence of at least portion of the template nucleic acid.

19. The method of claim 18, wherein each different 2'-modified reversible terminator nucleotide is added sequentially until a signal indicative of sequence specific incorporation of the correct 2'-modified reversible terminator nucleotide into the extended product is detected.

20. The method of claim 18, wherein each different 2'-modified reversible terminator nucleotide is added simultaneously and each different 2'-modified reversible terminator nucleotide is labeled with a different labeling moiety.

21. A method of sequencing at least a portion of a template nucleic acid, comprising:
   a) incubating the template nucleic acid in a reaction mixture comprising a primer, a polymerase, and a plurality of different 2'-modified reversible terminator nucleotides, each different 2'-modified reversible terminator nucleotide comprising one of the four naturally occurring bases or analogs thereof and further comprising a phosphate at the 2' position of the sugar moiety that terminates synthesis, under conditions in which the primer anneals to the template nucleic acid and is extended by the polymerase present in the reaction to form an extended product;
   b) determining if a signal indicative of sequence specific incorporation of the correct 2'-modified reversible terminator nucleotide into the extended product is present;
   c) if the signal is not present, repeating steps a) and b) with a different 2'-modified reversible terminator nucleotide, said different 2'-modified reversible terminator nucleotide comprising a different one of the four naturally occurring bases or analogs thereof,
   d) incubating the extended product with an enzyme that removes the phosphate at the 2' position present on the reversible terminator nucleotide, and
   e) repeating steps a) to d) a desired number of times to determine the sequence of at least a portion of the template nucleic acid.

* * * * *